(12) United States Patent  
Abbott et al.

(10) Patent No.: US 11,589,938 B2
(45) Date of Patent: Feb. 28, 2023

(54) COMPUTER-ASSISTED TELE-OPERATED SURGERY SYSTEMS AND METHODS

(71) Applicant: Intuitive Surgical Operations, Inc., Sunnyvale, CA (US)

(72) Inventors: Ryan Charles Abbott, San Jose, CA (US); Daniel H. Gomez, Los Gatos, CA (US); Amy Kerdok, San Jose, CA (US); Ian E. McDowall, Woodside, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 92 days.

(21) Appl. No.: 17/246,008

(22) Filed: Apr. 30, 2021

(65) Prior Publication Data

US 2021/0251705 A1  Aug. 19, 2021

Related U.S. Application Data

(63) Continuation of application No. 16/325,978, filed as application No. PCT/US2017/048425 on Aug. 24, 2017, now Pat. No. 11,020,192.

(Continued)

(51) Int. Cl.
*A61B 34/35*  (2016.01)
*A61B 17/00*  (2006.01)

(Continued)

(52) U.S. Cl.
CPC .............. *A61B 34/35* (2016.02); *A61B 34/00* (2016.02); *A61B 34/37* (2016.02);

(Continued)

(58) Field of Classification Search
CPC .......... A61B 2017/00477; A61B 34/35; A61B 34/00; A61B 34/37; A61B 34/71;

(Continued)

(56) References Cited

U.S. PATENT DOCUMENTS 5,397,323 A  3/1995 Taylor et al.
6,451,027 B1  9/2002 Cooper et al.

(Continued)

FOREIGN PATENT DOCUMENTS

CN  102119872 A  7/2011
CN  102292046 A  12/2011

(Continued)

OTHER PUBLICATIONS

Extended European Search Report for Application No. EP17844421.2 dated Mar. 16, 2020, 9 pages.

(Continued)

*Primary Examiner* — Tan-Uyen T Ho
*Assistant Examiner* — Bridget E. Rabaglia
(74) *Attorney, Agent, or Firm* — Fish & Richardson P.C.

(57) ABSTRACT

Systems and methods for minimally invasive computer-assisted telesurgery are described. For example, this disclosure provides surgical instruments and instrument drive systems for computer-assisted tele-operated surgery that are structured and operated to negate the effects of cable stretch within the surgical instruments.

15 Claims, 10 Drawing Sheets

Related U.S. Application Data

(60) Provisional application No. 62/379,114, filed on Aug. 24, 2016, provisional application No. 62/379,112, filed on Aug. 24, 2016.

(51) Int. Cl.
*A61B 34/00* (2016.01)
*A61B 34/37* (2016.01)
*A61B 90/00* (2016.01)

(52) U.S. Cl.
CPC .............. *A61B 2017/00477* (2013.01); *A61B 2090/064* (2016.02); *A61B 2090/371* (2016.02)

(58) Field of Classification Search
CPC ... A61B 2034/715; A61B 34/72; A61B 34/73; A61B 34/30; A61B 2034/301; A61B 2034/302; A61B 2034/303; A61B 2034/304; A61B 2034/305; A61B 34/70
See application file for complete search history.

(56) References Cited

U.S. PATENT DOCUMENTS

| | | | |
|---|---|---|---|
| 7,391,173 B2 | 6/2008 | Schena | |
| 8,151,661 B2 | 4/2012 | Schena et al. | |
| 8,852,174 B2 | 10/2014 | Burbank | |
| 8,968,312 B2 | 3/2015 | Marczyk et al. | |
| 9,713,509 B2 | 7/2017 | Schuh et al. | |
| 9,993,313 B2 | 6/2018 | Schuh et al. | |
| 10,786,329 B2 | 9/2020 | Schuh et al. | |
| 11,020,192 B2 | 6/2021 | Abbott et al. | |
| 2003/0040758 A1 | 2/2003 | Wang et al. | |
| 2005/0228365 A1 | 10/2005 | Wang et al. | |
| 2010/0204713 A1 | 8/2010 | Ruiz Morales | |
| 2011/0213383 A1 | 9/2011 | Lee et al. | |
| 2013/0172713 A1 | 7/2013 | Kirschenman | |
| 2014/0005718 A1* | 1/2014 | Shelton, IV | A61B 34/30 606/205 |
| 2015/0173840 A1 | 6/2015 | Lohmeier | |
| 2016/0213438 A1 | 7/2016 | Jogasaki et al. | |
| 2016/0235490 A1 | 8/2016 | Srivastava et al. | |
| 2016/0360949 A1 | 12/2016 | Hyodo et al. | |
| 2017/0020615 A1 | 1/2017 | Koenig et al. | |
| 2018/0049737 A1 | 2/2018 | Swayze et al. | |
| 2018/0353252 A1* | 12/2018 | Chassot | A61B 34/71 |
| 2019/0175294 A1 | 6/2019 | Abbott et al. | |

FOREIGN PATENT DOCUMENTS

| | | |
|---|---|---|
| EP | 2415418 A1 | 2/2012 |
| JP | H11507252 A | 6/1999 |
| WO | WO-2010039387 A1 | 4/2010 |
| WO | WO-2012049623 A1 | 4/2012 |
| WO | WO-2013025831 A2 | 2/2013 |
| WO | WO-2014138365 A1 | 9/2014 |
| WO | WO-2015175200 A1 | 11/2015 |
| WO | WO-2016043845 A1 | 3/2016 |
| WO | WO-2016064616 A1 | 4/2016 |
| WO | WO-2016090459 A1 | 6/2016 |
| WO | WO-2016144998 A1 | 9/2016 |
| WO | WO-2016183054 A1 | 11/2016 |

OTHER PUBLICATIONS

International Search Report and Written Opinion for Application No. PCT/US2017/048425, dated Dec. 26, 2017, 11 pages.

International Search Report and Written Opinion for Application No. PCT/US2017/051846, dated Jan. 10, 2018, 11 pages.

Long J.A., et al., "Development of Miniaturized Light Endoscope-holder Robot for Laparoscopic Surgery," Journal of Endourology, Aug. 2007, vol. 21 (8), pp. 911-914.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

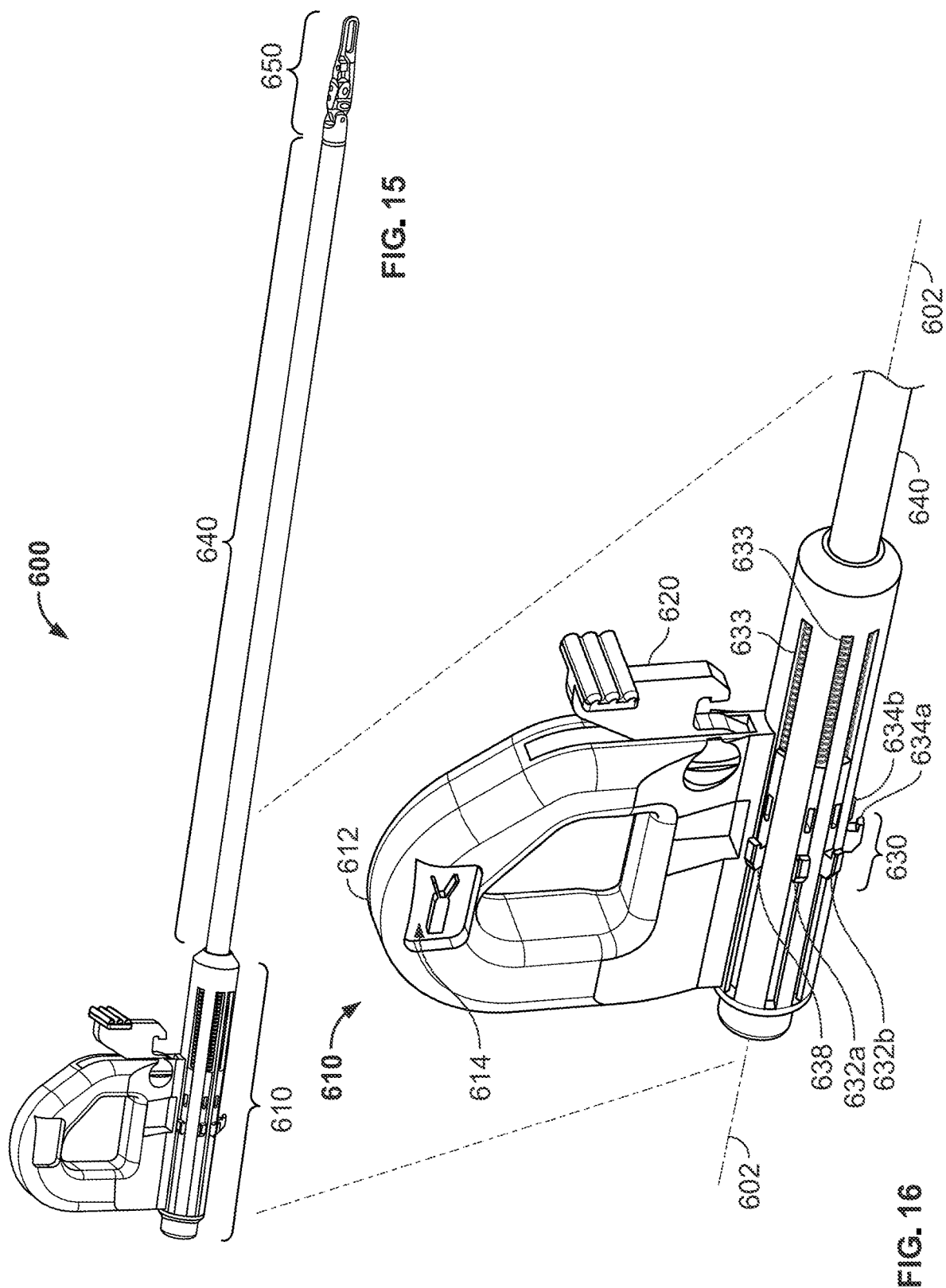

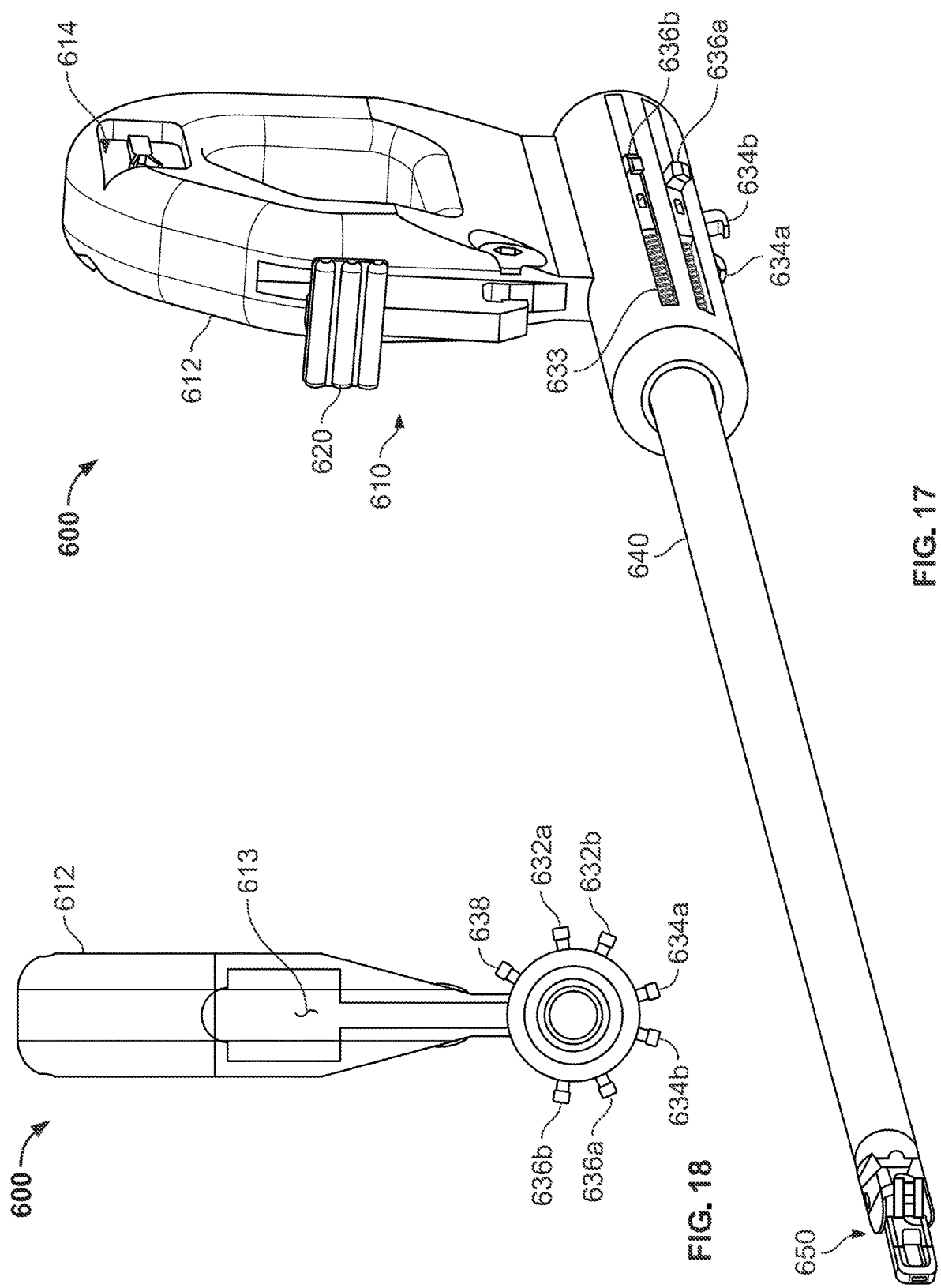

COMPUTER-ASSISTED TELE-OPERATED SURGERY SYSTEMS AND METHODS

RELATED APPLICATIONS

This application is a continuation of U.S. patent application Ser. No. 16/325,978 (filed on Feb. 15, 2019), which claims the benefit of International Patent Application No. PCT/US2017/048425 (filed on Aug. 24, 2017), which claims the benefit of priority to U.S. Provisional Patent Applications No. 62/379,112 (filed Aug. 24, 2016) and 62/379,114 (filed Aug. 24, 2016). Each of the foregoing applications are incorporated herein by reference in their entirety.

TECHNICAL FIELD

This disclosure relates to devices and methods for minimally invasive computer-assisted tele-operated surgery. For example, this disclosure relates to surgical instruments for computer-assisted tele-operated surgery that are structured to negate the effects of cable stretch.

BACKGROUND

Teleoperated surgical systems (often called "robotic" surgical systems because of the use of robot technology) and other computer-assisted devices often include one or more instrument manipulators to manipulate instruments for performing a task at a surgical work site and at least one manipulator for supporting an image capturing device which captures images of the surgical work site. A manipulator arm comprises a plurality of links coupled together by one or more actively controlled joints. In many embodiments, a plurality of actively controlled joints may be provided. The robot arm may also include one or more passive joints, which are not actively controlled, but which comply with movement of an actively controlled joint. Such active and passive joints may be various types, including revolute or prismatic joints. The kinematic pose of the manipulator arm and its associated instrument or image capture device may be determined by the positions of the joints and knowledge of the structure and coupling of the links and the application of known kinematic calculations.

Minimally invasive telesurgical systems for use in surgery are being developed to increase a surgeon's dexterity as well as to allow a surgeon to operate on a patient from a remote location. Telesurgery is a general term for surgical systems in which the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a stereoscopic image of the surgical site that provides the illusion of depth on a suitable viewer or display, the surgeon performs the surgical procedures on the patient by manipulating master control input devices, which in turn control the motion of corresponding teleoperated instruments. The teleoperated surgical instruments can be inserted through small, minimally invasive surgical apertures or natural orifices to treat tissues at surgical sites within the patient, often avoiding the trauma generally associated with accessing a surgical worksite by open surgery techniques. These computer-assisted tele-operated systems can move the working ends (end effectors) of the surgical instruments with sufficient dexterity to perform quite intricate surgical tasks, often by pivoting shafts of the instruments at the minimally invasive aperture, sliding of the shaft axially through the aperture, rotating of the shaft within the aperture, and the like.

SUMMARY

This disclosure provides devices and methods for minimally invasive robotic surgery using a computer-assisted tele-operated surgery device. For example, this disclosure relates to surgical instruments for computer-assisted tele-operated surgery that are structured to negate the effects of cable stretch. The devices and methods provided herein can be used in conjunction with computer-assisted tele-operated surgery systems (also referred to herein as "robotic surgery systems") that use either hardware-constrained remote centers of motion or software-constrained remote centers of motion.

In one aspect, a medical device includes a surgical instrument and a drive unit for the surgical instrument. A first actuator in the drive unit is in a non-detained engagement with a first engagement member of the instrument, and a second actuator in the drive unit is in a non-detained engagement with a second engagement member of the instrument. The first and second engagement members of the instrument are coupled to the instrument's end effector, so that the end effector moves as the first and second engagement members move. In a further aspect, the drive unit includes an instrument shaft actuator, the instrument includes a shaft actuator engagement member, and the instrument shaft actuator and the shaft actuator engagement member may be in either a non-detained or a detained engagement.

In one aspect, a surgical instrument includes an end effector, a first engagement member coupled to the end effector, and a second engagement member coupled to the end effector. The first and second engagement members are configured to be in a non-detained engagement with corresponding first and second actuators of a drive unit for the surgical instrument. In a further aspect, the instrument includes a shaft actuator engagement member that is configured to be in either a non-detained or a detained engagement with a corresponding instrument shaft actuator of the drive unit.

In one aspect, the disclosure is directed to a surgical instrument for a computer-assisted tele-operated surgery system. The surgical instrument includes: a proximal end portion; an instrument shaft extending from the proximal end portion (the instrument shaft including a distal end portion opposite from the proximal end portion); an end effector coupled to the distal end portion (the end effector having at least a first degree of freedom whereby the end effector is movable relative to the instrument shaft); a first tensioning member coupled to the end effector and extending along the instrument shaft; and a second tensioning member coupled to the end effector and extending along the instrument shaft. The second tensioning member terminates at a second actuator engagement member. The second actuator engagement member is movably coupled to the proximal end portion. The instrument shaft defines a longitudinal axis of the surgical instrument. The first tensioning member terminates at a first actuator engagement member. The first actuator engagement member is movably coupled to the proximal end portion. Moving the first actuator engagement member proximally moves the second actuator engagement member distally and moves the end effector in a first manner relative to the instrument shaft. The first manner comprises movement facilitated by the first degree of freedom. Moving the second actuator engagement member proximally moves the first actuator engagement member distally and moves the end effector in a second manner relative to the instrument shaft. The second manner is facilitated by the first degree of freedom and opposes the first manner. The first actuator engagement member and the second actuator engagement member are positionable at a same longitudinal location along the longitudinal axis of the surgical instrument.

Such a surgical instrument may optionally include one or more of the following features. The proximal end portion may include a handle configured to facilitate manual gripping and manipulation of the surgical instrument. The handle may extend radially from the longitudinal axis in relation to other portions of the proximal end portion. The handle may include an RFID chip for storing information pertaining to the surgical instrument. The handle may include an indicium identifying a type of surgical instrument. The surgical instrument may also include an instrument shaft actuator engagement member coupled to the proximal end portion. The instrument shaft actuator engagement member may include a latch mechanism. The first actuator engagement member and the second actuator engagement member may each be slidably coupled to the proximal end portion. The surgical instrument may also include one or more pre-load tensioning members that tension the first tensioning member and the second tensioning member. The one or more pre-load tensioning members may each comprise a spring. The first tensioning member and the second tensioning member may each comprise a cable. The end effector may have at least a second degree of freedom. The surgical instrument may also include: a third tensioning member coupled to the end effector and extending along the instrument shaft (the third tensioning member may terminate at a third actuator engagement member and may be movably coupled to the proximal end portion); and a fourth tensioning member coupled to the end effector and extending along the instrument shaft (the fourth tensioning member may terminate at a fourth actuator engagement member and may be movably coupled to the proximal end portion). Moving the third actuator engagement member proximally may move the fourth actuator engagement member distally and may move the end effector in a third manner relative to the instrument shaft (the third manner comprising movement facilitated by the second degree of freedom). Moving the fourth actuator engagement member proximally may move the third actuator engagement member distally and may move the end effector in a fourth manner relative to the instrument shaft (the fourth manner facilitated by the second degree of freedom and opposing the third manner). In some embodiments, each of: (i) the first actuator engagement member, (ii) the second actuator engagement member, (iii) the third actuator engagement member, and (iv) the fourth actuator engagement member are positionable at a same longitudinal location along the longitudinal axis of the surgical instrument. The third actuator engagement member and the fourth actuator engagement member may be each slidably coupled to the proximal end portion.

In another aspect, the disclosure is directed to a surgical instrument for a computer-assisted tele-operated surgery system. The surgical instrument includes: a proximal end portion; an instrument shaft extending from the proximal end portion (the instrument shaft includes a distal end portion opposite from the proximal end portion and defines a longitudinal axis of the surgical instrument); an end effector coupled to the distal end portion (the end effector has at least a first degree of freedom whereby the end effector is movable relative to the instrument shaft); a first tensioning member coupled to the end effector and extending along the instrument shaft (the first tensioning member terminates at a first actuator engagement member that is movably coupled to the proximal end portion); a second tensioning member coupled to the end effector and extending along the instrument shaft (the second tensioning member terminates at a second actuator engagement member that is movably coupled to the proximal end portion); and an instrument shaft actuator engagement member that is coupled to the proximal end portion. Moving the first actuator engagement member proximally moves the second actuator engagement member distally and moves the end effector in a first manner relative to the instrument shaft. The first manner includes movement facilitated by the first degree of freedom. Moving the second actuator engagement member proximally moves the first actuator engagement member distally and moves the end effector in a second manner relative to the instrument shaft. The second manner is facilitated by the first degree of freedom and opposes the first manner. The first actuator engagement member and the second actuator engagement member are each configured for facilitating movements of the end effector in response to receiving a proximally-directed force, and are each not configured for facilitating movements of the end effector in response to receiving a distally-directed force. The instrument shaft actuator engagement member is configured for facilitating movements of the entire surgical instrument distally in response to receiving a distally-directed force.

Such a surgical instrument may optionally include one or more of the following features. The proximal end portion may include a handle configured to facilitate manual gripping and manipulation of the surgical instrument. The handle may extend radially from the longitudinal axis in relation to other portions of the proximal end portion. The handle may include an RFID chip for storing information pertaining to the surgical instrument and an indicium identifying a type of surgical instrument. The instrument shaft actuator engagement member may be configured for facilitating movements of the entire surgical instrument proximally in response to receiving a proximally-directed force. The instrument shaft actuator engagement member may include a latch mechanism. The first actuator engagement member and the second actuator engagement member may be each slidably coupled to the proximal end portion and may be each positionable at a same longitudinal location along the longitudinal axis of the surgical instrument. The surgical instrument may also include one or more pre-load tensioning members that tension the first tensioning member and the second tensioning member. The one or more pre-load tensioning members may each comprise a spring. The end effector may have at least a second degree of freedom. The surgical instrument may also include: a third tensioning member coupled to the end effector and extending along the instrument shaft (the third tensioning member may terminate at a third actuator engagement member that may be movably coupled to the proximal end portion); and a fourth tensioning member coupled to the end effector and extending along the instrument shaft (the fourth tensioning member may terminate at a fourth actuator engagement member that may be movably coupled to the proximal end portion). Moving the third actuator engagement member proximally may move the fourth actuator engagement member distally and may move the end effector in a third manner relative to the instrument shaft. The third manner may include movement facilitated by the second degree of freedom. Moving the fourth actuator engagement member proximally may move the third actuator engagement member distally and may move the end effector in a fourth manner relative to the instrument shaft. The fourth manner may be facilitated by the second degree of freedom and may oppose the third manner. The third actuator engagement member and the fourth actuator engagement member may be each configured to move the end effector in response to receiving a proximally-directed force, and may be each configured to not move the end effector in response to receiving a distally-directed force. In some embodiments, each of: (i) the first actuator engagement member, (ii) the second actuator engagement member, (iii) the third actuator engagement member, and (iv) the fourth actuator engagement member may be positionable at a same longitudinal location along the longitudinal axis of the surgical instrument.

In another aspect, the disclosure is directed to a surgical instrument and an instrument drive system configured to be selectively coupled with the surgical instrument by moving the surgical instrument distally along the longitudinal axis into releasable engagement with the instrument drive system. The surgical instrument includes: a proximal end portion; an instrument shaft extending from the proximal end portion (the instrument shaft includes a distal end portion opposite from the proximal end portion and defines a longitudinal axis of the surgical instrument); an end effector mounted to the distal end portion (the end effector has at least a first degree of freedom whereby the end effector is movable relative to the instrument shaft); a first tensioning member coupled to the end effector and extending along the instrument shaft; and a second tensioning member coupled to the end effector and extending along the instrument shaft. The instrument drive system includes: a first actuator for tensioning the first tensioning member with a first tensile force that can move the end effector in a first manner relative to the instrument shaft (the first manner including movement facilitated by the first degree of freedom); a second actuator for tensioning the second tensioning member with a second tensile force that can move the end effector in a second manner relative to the instrument shaft (the second manner facilitated by the first degree of freedom and opposing the first manner); and a shaft actuator for applying a force to the instrument shaft (the force to the instrument shaft being directionally opposite to the first tensile force and to the second tensile force).

Such a surgical instrument system may optionally include one or more of the following features. The proximal end portion may include a handle configured to facilitate manual gripping and manipulation of the surgical instrument. The handle may extend radially from the longitudinal axis and may extend farther radially than adjacent portions of the instrument drive system while the surgical instrument is coupled with the instrument drive system. The selective coupling of the instrument drive system and the surgical instrument may be facilitated by the instrument drive system slidably receiving the surgical instrument is moved distally along the longitudinal axis. The surgical instrument may also include an instrument shaft actuator engagement member to which the shaft actuator releasably couples. The instrument shaft actuator engagement member may include a latch mechanism. The latch mechanism may extend radially from the longitudinal axis and may extend farther radially than adjacent portions of the instrument drive system while the surgical instrument is coupled with the instrument drive system. The first tensioning member may terminate at a first actuator engagement member that is slidably coupled to the proximal end portion. The second tensioning member may terminate at a second actuator engagement member that is slidably coupled to the proximal end portion. The first actuator may be selectively coupleable with the first actuator engagement member. The second actuator may be selectively coupleable with the second actuator engagement member. The first tensile force and the second tensile force may be parallel along the instrument shaft and directed toward the proximal end. The force to the instrument shaft may be directed along the instrument shaft toward the distal end portion. The end effector may move in the first manner relative to the instrument shaft when the first tensile force is greater than the second tensile force. The end effector may move in the second manner that may be in opposition to the first manner when the second tensile force is greater than the first tensile force. The instrument shaft may move distally in relation to the instrument drive system when the force to the instrument shaft is greater than a sum of the first tensile force plus the second tensile force. The instrument shaft may move proximally in relation to the instrument drive system when the force to the instrument shaft is less than the sum of the first tensile force plus the second tensile force. The end effector may have at least a second degree of freedom. The surgical instrument may also include: a third tensioning member coupled to the end effector and extending along the instrument shaft; a third actuator for tensioning the third tensioning member with a third tensile force that can move the end effector in a third manner relative to the instrument shaft (the third manner may include movement facilitated by the second degree of freedom); a fourth tensioning member coupled to the end effector and extending along the instrument shaft; and a fourth actuator for tensioning the fourth tensioning member with a fourth tensile force that can move the end effector in a fourth manner relative to the instrument shaft (the fourth manner may be facilitated by the second degree of freedom and may oppose the third manner). The end effector may move in the third manner relative to the instrument shaft when the third tensile force is greater than the fourth tensile force. The end effector may move in the fourth manner that is in opposition to the third manner when the fourth tensile force is greater than the third tensile force. The instrument shaft may move distally in relation to the instrument drive system when the force to the instrument shaft is greater than a sum of the first tensile force plus the second tensile force plus the third tensile force plus the fourth tensile force. The instrument shaft may move proximally in relation to the instrument drive system when the force to the instrument shaft is less than the sum of the first tensile force plus the second tensile force plus the third tensile force plus the fourth tensile force. The surgical instrument system may also include one or more pre-load tensioning members that tension the first tensioning member and the second tensioning member while the first actuator and the second actuator are not tensioning the first tensioning member and the second tensioning member, respectively. The one or more pre-load tensioning members may each comprise a spring. The surgical instrument system may also include: a first force sensor for detecting the first tensile force; a second force sensor for detecting the second tensile force; and an instrument shaft force sensor for detecting the force to the instrument shaft. Each of the first actuator, the second actuator, and the shaft actuator may be linear actuators comprising lead screws. In some embodiments, an entirety of the surgical instrument system is configured to roll about the longitudinal axis.

Some or all of the embodiments described herein may provide one or more of the following advantages. In some cases, the tele-operated surgical instruments provided herein are advantageously structured to negate the effects of cable stretch. Cables within conventional tele-operated surgical instruments are pre-tensioned during manufacturing, but the tensions may tend to decrease over time because the cables may stretch as the instruments are used. Such tension decreases can contribute to a lessening in the accuracy of control of the tele-operated surgical instruments in some cases. Additionally, autoclave sterilization of the tele-operated surgical instruments using heat and humidity can exacerbate cable stretch and losses of cable tension. The tele-operated surgical instruments provided herein advantageously compensate for cable stretch without a loss in the accuracy of control of the instruments. In addition, while the tele-operated surgical instruments provided herein are not in use, the tension on the cables is advantageously less than the tension during operation of the instrument. Further, the tele-operated surgical instruments provided herein advantageously compensate for manufacturing tolerances that pertain to cable tension. In result, the manufacturing processes of the instruments can be streamlined and made more cost effective.

In addition, the tele-operated surgical instruments provided herein are advantageously structured to interface with an instrument drive system that is compact, and has a relatively low mass and inertia. In addition, the mass distribution is substantially constant such that the inertia is substantially constant and therefore predictable.

Still further, in some embodiments the tele-operated surgical instruments provided herein are advantageously structured to interface with an instrument drive system in a manner that is readily detachable. For example, in some embodiments the surgical instrument can be detached from an instrument drive system merely by actuating a latch mechanism and retracting the instrument proximally out of engagement with the drive system. Such a readily detachable interface between the surgical instrument and the instrument drive system can provide advantages such as quick instrument removal in the event of an emergency, and user convenience during general change-outs of one surgical instrument for another.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 15 is a perspective view of an example surgical instrument that is configured in accordance with the schematic diagram of FIG. 9.

FIG. 16 is a perspective view of a proximal end portion of the surgical instrument of FIG. 15.

FIG. 17 is another perspective view of the surgical instrument of FIG. 15.

FIG. 18 is a proximal end view of the surgical instrument of FIG. 15.

Like reference symbols in the various drawings indicate like elements.

DETAILED DESCRIPTION

Figure 2:
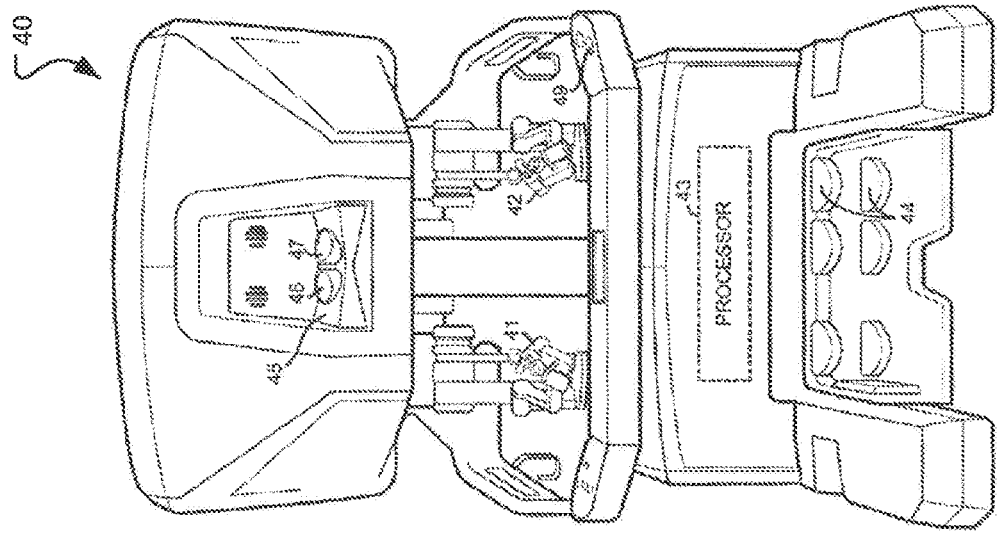
FIG. 2 is a front view of an example surgeon control unit of a computer-assisted tele-operated surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different locations (i.e., translational placements) and orientations (i.e., rotational placements) of a device in use or operation in addition to the location and orientation shown in the figures. For example, if a device in the figures is turned over, elements described as "below" or "beneath" other elements or features would then be "above" or "over" the other elements or features. Thus, the exemplary term "below" can encompass both locations and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device locations and orientations. The combination of a body's location and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

An example of a teleoperated surgical system is the da Vinci® Surgical System, commercialized by Intuitive Surgical, Inc. of Sunnyvale, Calif. Inventive aspects are associated with computer-assisted teleoperated surgical systems. Knowledgeable persons will understand that inventive aspects disclosed herein may be embodied and implemented in various ways, including computer-assisted and hybrid combinations of manual and computer-assisted embodiments and implementations. As applicable, inventive aspects may be embodied and implemented in both relatively smaller, hand-held, hand-operated devices and relatively larger systems that have additional mechanical support, as well as in other embodiments of computer-assisted teleoperated medical devices. In addition, inventive aspects are associated with advances in computer-assisted surgical systems that include autonomous rather than teleoperated actions, and so both teleoperated and autonomous surgical systems are included, even though the description concentrates on teleoperated systems.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both centralized single-location and distributed implementations.

This disclosure provides improved surgical and telesurgical devices, systems, and methods. The inventive concepts are particularly advantageous for use with telesurgical systems in which a plurality of surgical tools or instruments are mounted on and moved by an associated plurality of teleoperated manipulators during a surgical procedure. The teleoperated surgical systems will often comprise tele-robotic, telesurgical, and/or telepresence systems that include processors configured as master-slave controllers. By providing teleoperated surgical systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators to inhibit interference or collisions between these moving structures, and the like.

The manipulator assemblies described herein will often include a teleoperated manipulator and a tool mounted thereon (the tool often comprising a surgical instrument in surgical versions), although the term "manipulator assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a telesurgical procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. As used herein, the term "end effector" therefore includes but is not limited to the function of changing the orientation or position (e.g., a "wrist" function, a parallel motion function) of its distal-most part or parts (e.g., jaw(s) and the like).

When used for minimally invasive teleoperated surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

Figure 1:
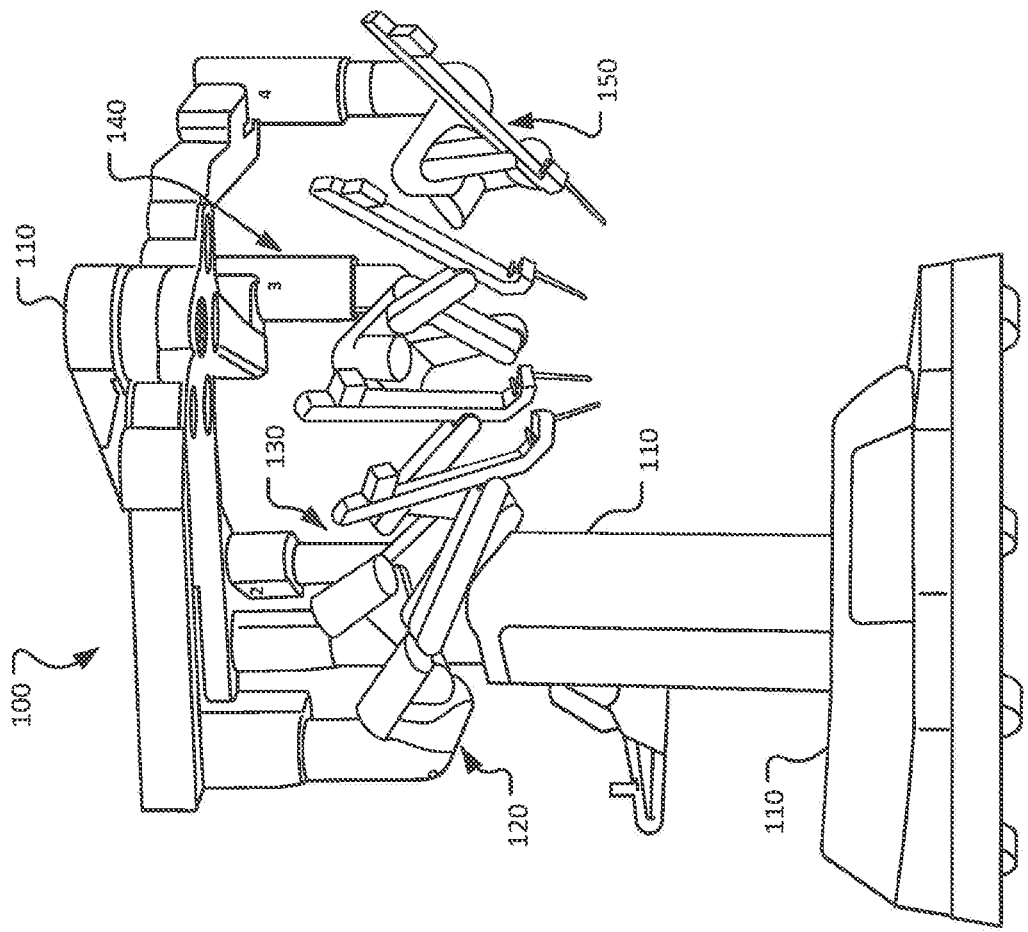
FIG. 1 is a perspective view of an example patient-side unit of a computer-assisted tele-operated surgery system.

Referring to FIGS. 1 and 2, systems for minimally invasive computer-assisted telesurgery (as referred to herein as "minimally invasive robotic surgery") can include a patient-side unit 100 and a surgeon control unit 40. Telesurgery is a general term for surgical systems where the surgeon uses some form of remote control, e.g., a servomechanism, or the like, to manipulate surgical instrument movements by using robot technology rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side unit 100 includes a base 110, a first robotic manipulator arm assembly 120, a second robotic manipulator arm assembly 130, a third robotic manipulator arm assembly 140, and a fourth robotic manipulator arm assembly 150. As shown, the base 110 includes a portion that rests on the floor, a vertical column, and a horizontal boom, and other base configurations to mechanically ground the patient-side unit may optionally be used. Each robotic manipulator arm assembly 120, 130, 140, and 150 is pivotably coupled to the base 110. In some embodiments, fewer than four or more than four robotic manipulator arm assemblies may be included as part of the patient-side unit 100. While in the depicted embodiment the base 110 includes casters to allow ease of mobility, in some embodiments the patient-side unit 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device (tool; surgical instrument) so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces 46 and 47 are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals. Additional input to the system may be made via one or more other inputs, such as buttons, touch pads, voice, and the like, as illustrated by input 49.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although described as a processor, it is to be appreciated that the processor 43 may be implemented by any combination of hardware, software, and firmware. Also, its functions as described herein may be performed by one unit or divided up among a number of subunits, each of which may be implemented in turn by any combination of hardware, software, and firmware. Further, although being shown as part of or being physically adjacent to the surgeon control unit 40, the processor 43 may also be distributed as subunits throughout the telesurgery system. Accordingly, control aspects referred to herein are implemented via processor 43 in either a centralized or distributed form.

Figure 3:
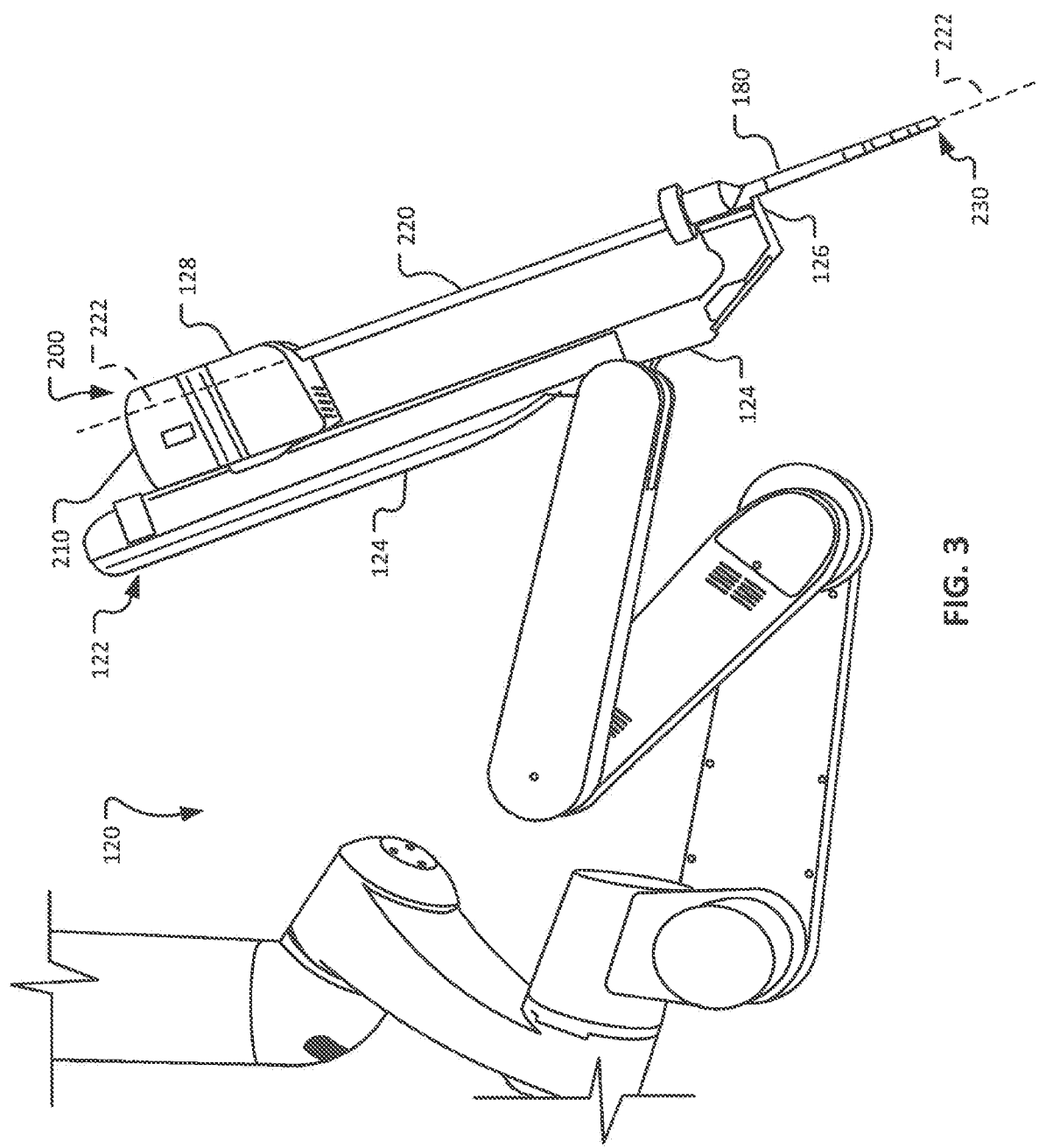
FIG. 3 is a side view of an example manipulator arm assembly of a computer-assisted tele-operated surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably coupleable with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
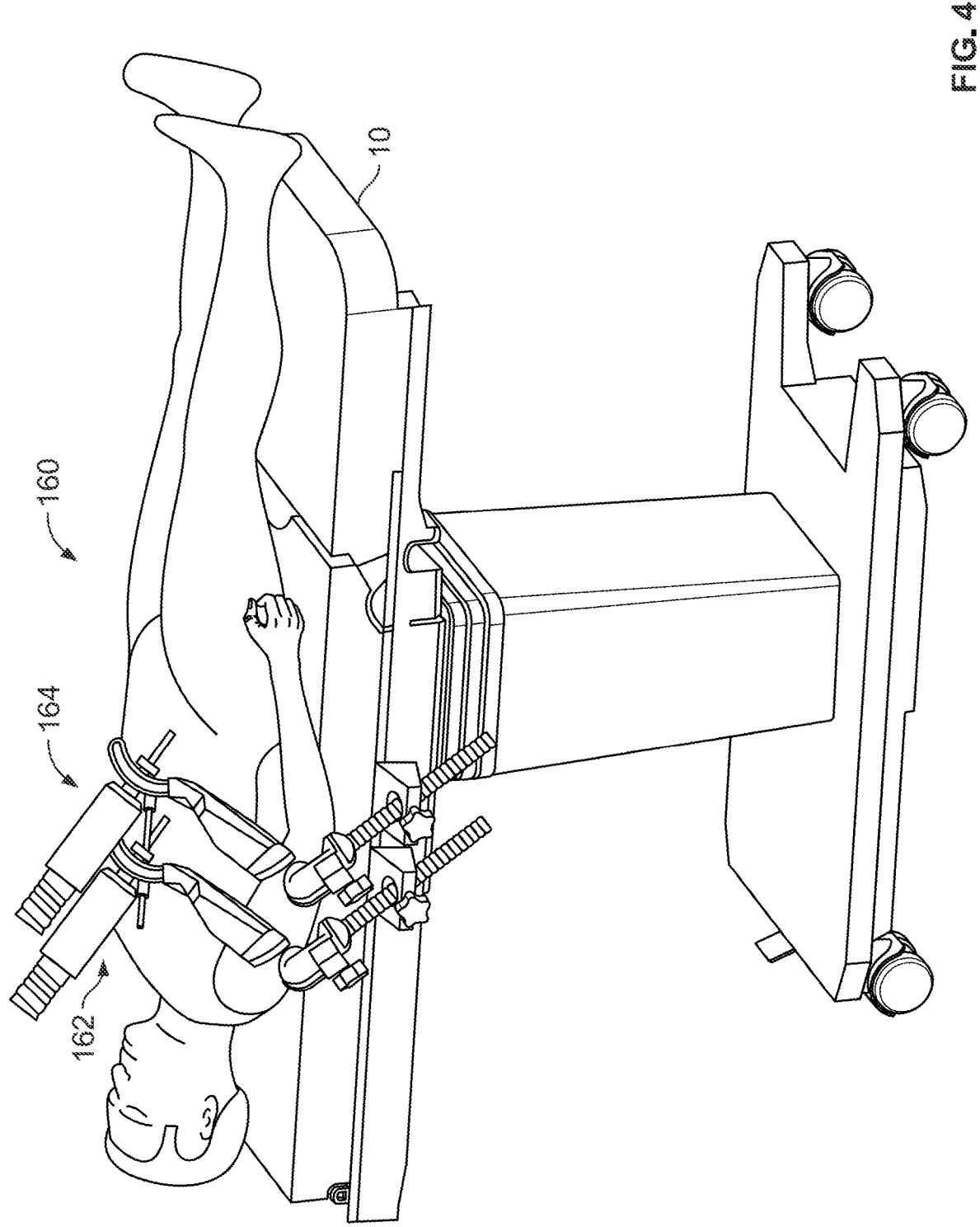
FIG. 4 is a perspective view of another type of patient-side computer-assisted tele-operated surgery system.

Also referring to FIG. 4, another example patient-side system 160 for minimally invasive computer-assisted tele-operated surgery includes a first robotic manipulator arm assembly 162 and a second robotic manipulator arm assembly 164 that are each mounted to an operating table 10. In some cases, this configuration of patient-side system 160 can be used as an alternative to the patient-side unit 100 of FIG. 1. While only two robotic manipulator arm assemblies 162 and 164 are depicted, it should be understood that more than two (e.g., three, four, five, six, and more than six) can be included in some configurations.

In some cases, the operating table 10 may be moved or reconfigured during the surgery. For example, in some cases, the operating table 10 may be tilted about various axes, raised, lowered, pivoted, rotated, and the like. In some cases, by manipulating the orientation of the operating table 10, the clinicians can utilize the effects of gravity to position internal organs of the patient in positions that facilitate enhanced surgical access. In some cases, such movements of the operating table 10 may be integrated as a part of the computer-assisted tele-operated surgery system, and controlled by the system.

Figure 5:
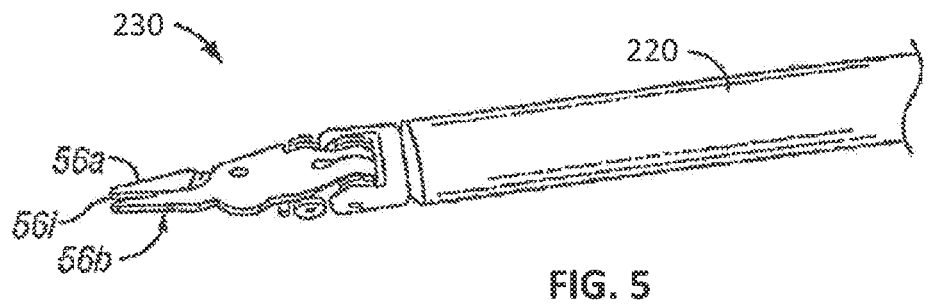
FIG. 5 is a perspective view of a distal end portion of an example surgical instrument in a first pose.
Figure 6:
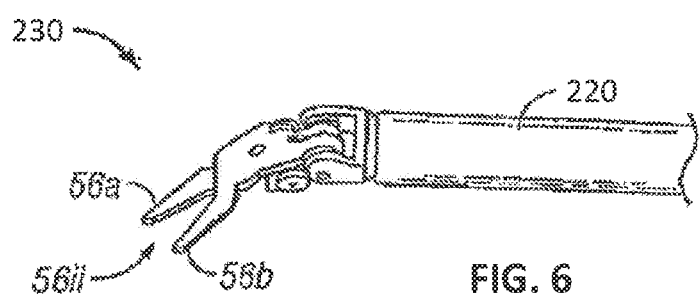
FIG. 6 is a perspective view of the distal end portion of the surgical instrument of FIG. 5 in a second pose.
Figure 7:
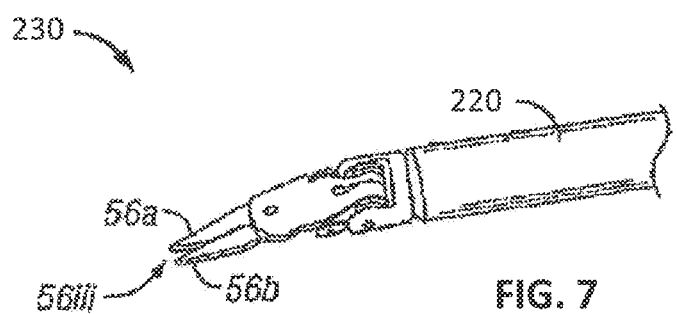
FIG. 7 is a perspective view of the distal end portion of the surgical instrument of FIG. 5 in a third pose.

Also referring to FIGS. 5-7, a variety of alternative computer-assisted tele-operated surgical instruments of different types and differing end effectors 230 may be used, with the instruments of at least some of the manipulators being removed and replaced during a surgical procedure. Several of these end effectors, including, for example, DeBakey Forceps 56*i*, microforceps 56*ii*, and Potts scissors 56*iii* include first and second end effector elements 56*a*, 56*b* which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42.

In some cases, the computer-assisted tele-operated surgical instruments include multiple degrees of freedom such as, but not limited to, roll, pitch, yaw, insertion depth, opening/closing of jaws, actuation of staple delivery, activation of electro-cautery, and the like. At least some of such degrees of freedom can be actuated by an instrument drive system to which the surgical instrument can be selectively coupled.

In some embodiments, the computer-assisted tele-operated surgical instruments include end effectors with two individually movable components such as, but not limited to, opposing jaws designed for grasping or shearing. When a first one of the individually movable components is moved as a second one of the individually movable components remains generally stationary or is moved in an opposing manner, the end effector can perform useful motions such as opening and closing for grasping, shearing, releasing, and the like. When the two components are moved synchronously in the same direction, speed and distance, the resulting motion is a type of pitch or yaw movement of the end effector. Hence, in some surgical instrument embodiments that have end effectors with two individually movable components, such as jaws, the arrangement can provide two degrees of freedom (e.g., pitch/yaw movements and opening/closing movements).

The elongate shaft 220 allow the end effector 230 and the distal end of the shaft 220 to be inserted distally into a surgical worksite through a minimally invasive aperture (via cannula 180), often through a body wall (e.g., abdominal wall) or the like. In some cases, a body wall retractor member on a distal end of the cannula 180 can be used to tent the body wall, thereby increasing the surgical workspace size. In some cases the surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 50. Hence, the robotic manipulator arm assemblies 120, 130, 140, and 150 will often undergo significant movement outside patient during a surgical procedure.

Figure 8:
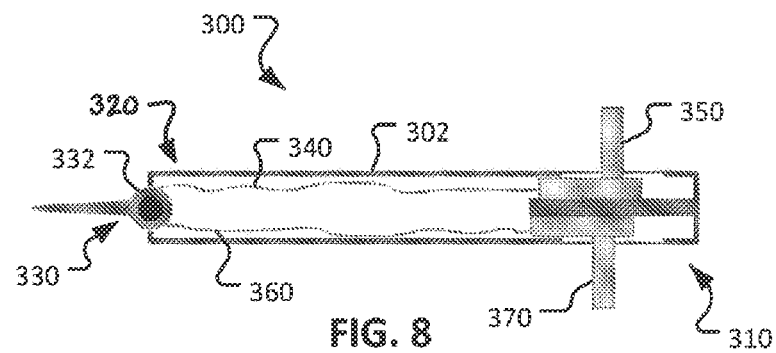
FIG. 8 is a simplified schematic diagram of an example tele-operated surgical instrument in accordance with some embodiments.

Referring to FIG. 8, an example surgical instrument 300 that can be used as part of a computer-assisted tele-operated surgery system is schematically depicted. The surgical instrument 300 includes an instrument shaft 302 (similar to shafts 220, 640) having a proximal (away from the surgical site) end portion 310 and a distal (toward the surgical site) end portion 320 opposite from the proximal end portion 310. The surgical instrument 300 also includes an end effector 330 (similar to end effectors 230, 650). In this schematic diagram, the end effector 330 is depicted as having a single degree of freedom in relation to the instrument shaft 302 (i.e., a freedom to yaw the end effector 330 in a rotary or pivoting fashion). It should be understood, however, that the end effectors 330 of the surgical instruments described herein can have more than one degree of freedom (e.g., two, three, four, five, six, or more than six degrees of freedom). Moreover, it should be understood that the concepts described in the context of the single degree of freedom of the end effector 330 can be extended to each degree of freedom of multiple degrees of freedom of the surgical instrument 300 and of other types of surgical instruments for computer-assisted tele-operated surgery systems.

Example surgical instrument 300 also includes a first tensioning member 340, a first actuator engagement member 350, a second tensioning member 360, and a second actuator engagement member 370. The first tensioning member 340 is coupled to the end effector 330 and extends along the instrument shaft 302 where it terminates at the first actuator engagement member 350. Similarly, the second tensioning member 360 is coupled to the end effector 330 and extends along the instrument shaft 302 where it terminates at the second actuator engagement member 370. The first actuator engagement member 350 and the second actuator engagement member 370 are movably coupled to the proximal end portion 310 of the surgical instrument. In some embodiments, the first actuator engagement member 350 and the second actuator engagement member 370 are slidably coupled to the proximal end portion 310 of the surgical instrument.

While the depicted embodiment includes sliding actuator engagement members 350 and 370, in some embodiments one or more other types of actuator engagement members can be included in the surgical instrument 300. For example, in some embodiments rotatable actuator engagement members are included. Such rotatable actuator engagement members can be coupled to capstans or pulleys that are engaged with the tensioning members 340 and 360. Rotation of the rotatable actuator engagement members can apply or relieve tension on the corresponding tensioning member 340 and 360. Accordingly, movements of the end effector 330 and tensioning of the tensioning member 340 and 360 can be controlled via rotatable actuator engagement members.

In some embodiments, some or all portions of the first tensioning member 340 and the second tensioning member 360 comprise flexible cables (e.g., without limitation, stranded tungsten cables, stainless steel cables, etc.). In some embodiments, the first tensioning member 340 and the second tensioning member 360 are different portions of a single continuous cable. In some embodiments, the first tensioning member 340 and the second tensioning member 360 are separate cables. The first tensioning member 340 and the second tensioning member 360 may additionally or alternatively include other components such as, but not limited to, hypo-tubes.

The first tensioning member 340 and the second tensioning member 360 are each coupled to the end effector 330. In the depicted embodiment, the first tensioning member 340 and the second tensioning member 360 are each coupled to the end effector 330 via a pulley 332 (which can be a capstan, crank arm, rotary drive member, etc.). Hence, a proximal movement of the first actuator engagement member 350 moves the second actuator engagement member 370 distally, and moves the end effector 330 in a first manner relative to the instrument shaft 302. Conversely, a proximal movement of the second actuator engagement member 370 moves the first actuator engagement member 350 distally, and moves the end effector 330 in a second manner relative to the instrument shaft 302. In this fashion, desired movements of the end effector 330 can be facilitated in a controlled manner. Moreover, as described further below, while the movements and/or pose of the end effector 330 is being controlled using actuator engagement members 350 and 370, the tensions in the tensioning members 340 and 360 can be concurrently controlled. In effect, two degrees of freedom (e.g., end effector 330 position and tensioning members 340 and 360 tension) of the surgical instrument 300 can be concurrently controlled in accordance with the devices and methods described herein.

The surgical instrument 300 is depicted here as being separated from an instrument drive system. Accordingly, in some embodiments the tension in the first tensioning member 340 and the second tensioning member 360 can be less than the tension used during the operation of the surgical instrument 300. In some cases, having a relatively low tension in the first tensioning member 340 and the second tensioning member 360 while the surgical instrument 300 is not in use can be advantageous (e.g., to reduce the potential for cable stretch). In some embodiments, pre-load tensioning members (e.g., springs, not shown) may be included in surgical instrument 300 to maintain a minimal tension in the first tensioning member 340 and the second tensioning member 360 while the surgical instrument 300 is separated from an instrument drive system. Such minimal pre-tensioning may help ensure that the first tensioning member 340 and the second tensioning member 360 remain oriented within the surgical instrument 300 as desired.

While the surgical instrument 300 is depicted as having a single degree of freedom, it should be understood that this is a simplified schematic diagram and that the surgical instrument 300 can have two or more degrees of freedom. The concepts described herein in reference to the single degree of freedom of surgical instrument 300 (as depicted) can be extrapolated to the two or more degrees of freedom of the surgical instruments provided herein. For example, when the end effector 330 includes two individually movable components, such as opposing jaws designed for grasping or shearing as described above, the arrangement provides two degrees of freedom (e.g., pitch/yaw movements when the components are moved synchronously and opening/closing movements when the components are moved asynchronously or in an opposing manner). Extending the concepts described in reference to the surgical instrument 300 to such an end effector would result in an instrument having four actuator engagement members and four tensioning members to actuate the two degrees of freedom.

Figure 9:
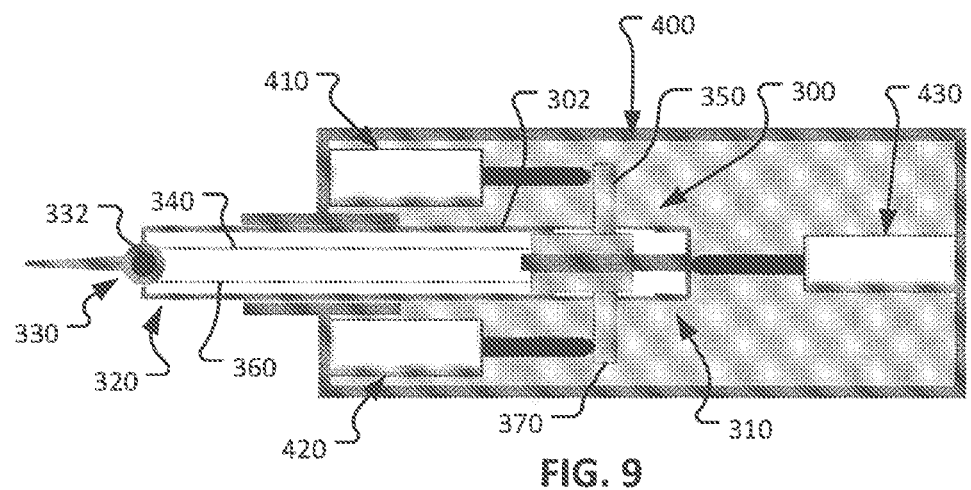
FIG. 9 is a schematic diagram of the tele-operated surgical instrument of FIG. 8 coupled with an example instrument drive system in accordance with some embodiments.

Referring to FIG. 9, the surgical instrument 300 can be selectively coupled with an instrument drive system 400. That is, the surgical instrument 300 can be coupled with the instrument drive system 400 for operation as part of a computer-assisted tele-operated surgery system. Additionally, the surgical instrument 300 can be uncoupled from the instrument drive system 400 (e.g., for replacement by another type of surgical instrument, for sterilization of the surgical instrument 300, etc.).

In some embodiments, the instrument drive system 400 can be mounted to a manipulator assembly, which can in turn be mounted to another structure or a base. The instrument drive system 400 can be interchangeably mounted to a manipulator assembly in some cases. That is, in some embodiments the instrument drive system 400 is designed for convenient detachment from a manipulator assembly such that it is readily interchangeable with another instrument drive system. Therefore, the instrument drive system 400 may also be referred to as a pod 400. As used herein, the term "pod" indicates the interchangeable aspects of some instrument drive systems in relation to a manipulator assembly—i.e., one pod may be removed from a manipulator assembly and replaced with a second pod of the same, similar, or different configuration. In some embodiments, the instrument drive system 400 is affixed to a manipulator assembly in such a way that the instrument drive system 400 is not readily detachable or interchangeable.

In some embodiments, the surgical instrument 300 is slidably coupleable with the instrument drive system 400. That is, the surgical instrument 300 can be slidably extended distally and slidably retracted proximally in relation to the instrument drive system 400.

In the depicted embodiment, the instrument drive system 400 includes a first actuator 410, a second actuator 420, and a shaft actuator 430. The first actuator 410 is releasably coupleable with the first actuator engagement member 350. Hence, the first actuator 410 can induce a tensile force in the first tensioning member 340. The second actuator 420 is releasably coupleable with the second actuator engagement member 370. Hence, the second actuator 420 can induce a tensile force in the second tensioning member 360. The actuators 410, 420 are shown in a non-detained engagement with the corresponding actuator engagement members 350, 370. Optionally, the actuators 410, 420 are in a detained engagement with the corresponding actuator engagement members 350, 370, such as a latch. In a detained engagement, two objects are fixed together (releasably or otherwise) so that as one object moves, the other object correspondingly moves. In a non-detained engagement, the two objects are not fixed together, so that if one object moves toward the other, the other object moves, but if one object moves away from the other, the other object will not move.

In light of the arrangement between the surgical instrument 300 and the first and second actuators 410 and 420 of the instrument drive system 400 as described above, it can be envisioned that concerted modulation of the forces exerted from the first and second actuators 410 and 420 to the first and second actuator engagement members 350 and 370, respectively, can result in controlled motion of the end effector 330 in its degree of freedom. Moreover, it can also be envisioned (as described further below), that the tensions in the first and second tensioning members 340 and 360 can also be controlled by the concerted modulation of the forces exerted from the first and second actuators 410 and 420 to the first and second actuator engagement members 350 and 370, respectively. Still further, it can also be envisioned that the tensions in the first and second tensioning members 340 and 360 can be controlled by the concerted modulation of the forces exerted from the first and second actuators 410 and 420 to the first and second actuator engagement members 350 and 370, respectively, while the concerted modulation of the forces exerted from the first and second actuators 410 and 420 to the first and second actuator engagement members 350 and 370 also concurrently cause desired movements of the end effector 330. Put more simply, the tensions in the first and second tensioning members 340 and 360 can be controlled to a desired amount of tensile force while movements of the end effector 330 are being made as desired. This concept can be referred to herein as "dynamic tension control" or "dynamic tension and position control."

Still referring to FIG. 9, the instrument drive system 400 also includes the shaft actuator 430 that engages with a corresponding shaft actuator engagement member on the surgical instrument in a non-detained or detained engagement. An example of non-detained engagement is engagement with a part of distal end portion 310 that acts as the shaft actuator engagement member, as shown. An example of detained engagement is engagement with a latch, as described below. The shaft actuator 430 releasably couples with the instrument shaft 302 for both detained and non-detained engagement.

In some embodiments, the shaft actuator 430 releasably couples with the instrument shaft 302 (or to a structure coupled to the instrument shaft 302) using a latch mechanism. Accordingly, in some such embodiments, while the shaft actuator 430 is latched to the instrument 300, the shaft actuator 430 is able to exert either a distally-directed force or a proximally-directed force to distally extend or proximally retract the instrument 300, as desired, in relation to the instrument drive system 400. It should be understood that such a latch mechanism for coupling the shaft actuator 430 to the instrument shaft 302 is not required in all embodiments. Further, in some embodiments the shaft actuator 430 is configured to only exert a distally-directed force to the instrument 300 (i.e., not a proximally-directed force). The dynamic tension and position control concepts described herein can still be performed while the shaft actuator 430 is configured to exert only a distally-directed force to the instrument 300.

The actuators 410, 420, and 430 can be various types of actuators. In some embodiments, the first actuator 410, a second actuator 420, and a shaft actuator 430 each comprise electrical motors that are coupled to lead screws that linearly drive nut members on the threads of the lead screw. In some embodiments, the entire assembly of the surgical instrument 300 in combination with the instrument drive system 400 can be driven together to result in a desired motion of the end effector, such as a rolling motion about the longitudinal axis of the surgical instrument 300.

Figure 10:
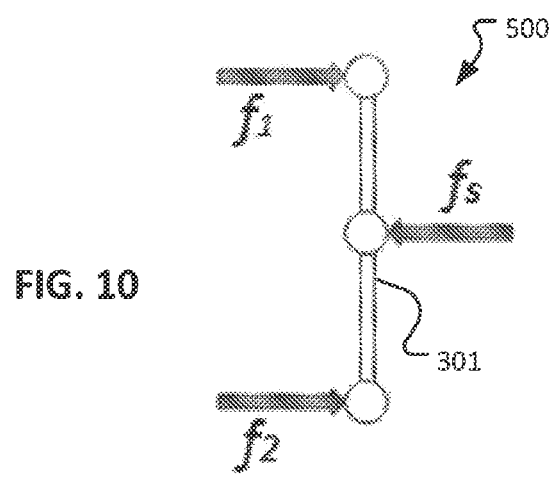
FIG. 10 is a force diagram pertaining to the instrument and drive system of FIG. 9.

Referring also to FIG. 10, a force diagram 500 can be used to further describe the structure and operations of the surgical instrument 300 in combination with the instrument drive system 400. The body 301 is representative of the surgical instrument 300. Force $f_1$ is representative of the force applied by the first actuator 410 to the first engagement member 350. Force $f_2$ is representative of the force applied by the second actuator 420 to the second engagement member 370. Force $f_s$ is representative of the force applied by the shaft actuator 430 to the instrument shaft 302.

Force $f_s$ is directionally opposite to forces $f_1$ and $f_2$. Hence, in a static context, force $f_s$ is equal to the sum of forces $f_1$ and $f_2$. In a dynamic context, if force $f_s$ is greater than the sum of forces $f_1$ and $f_2$, then the body 301 will move in the direction of force $f_s$. Conversely, if force $f_s$ is less than the sum of forces $f_1$ and $f_2$, then the body 301 will move in the direction of forces $f_1$ and $f_2$.

Applying the principles described above regarding the force diagram 500 to the analogous arrangement of the surgical instrument 300 in combination with the instrument drive system 400, the following concepts can be envisioned. While the surgical instrument 300 is in a constant spatial relationship with the instrument drive system 400 (i.e., in a static context), the sum of the forces exerted from the first and second actuators 410 and 420 to the first and second actuator engagement members 350 and 370 equal the force exerted from the shaft actuator 430 to the instrument shaft 302. In addition, while the sum of the forces exerted from the first and second actuators 410 and 420 to the first and second actuator engagement members 350 and 370 are greater than the force exerted from the shaft actuator 430 to the instrument shaft 302, the surgical instrument 300 will move proximally in relation to the instrument drive system 400. Still further, while the sum of the forces exerted from the first and second actuators 410 and 420 to the first and second actuator engagement members 350 and 370 are less than the force exerted from the shaft actuator 430 to the instrument shaft 302, the surgical instrument 300 will move distally in relation to the instrument drive system 400.

To be clear, the combinations of forces from the actuators 410, 420, and 430 that cause the proximal and distal movements of the surgical instrument 300 in relation to the instrument drive system 400 involve the sum of the forces exerted from the first and second actuators 410 and 420 to the first and second actuator engagement members 350 and 370. Hence, it can be envisioned that the forces exerted from the first and second actuators 410 and 420 to the first and second actuator engagement members 350 and 370 can be equal to each other, or can differ from each other while the sum is still a total amount that is appropriate to result in a desired distal/proximal movement and/or orientation between the surgical instrument 300 and the instrument drive system 400. For example, in the case when the forces exerted from the first and second actuators 410 and 420 to the first and second actuator engagement members 350 and 370 differ from each other, a movement of end effector 330 will result, and in the case when the forces exerted from the first and second actuators 410 and 420 to the first and second actuator engagement members 350 and 370 are equal to each other, the end effector 330 will be stationary in relation to the instrument shaft 302. Again, it should be understood that, using the structure and operational concepts provided herein, distal/proximal movements of the surgical instrument 300 in relation to the instrument drive system 400 can be made concurrently with movements of the end effector 300 in relation to the instrument shaft 302. Moreover, both such movements can be made concurrently while the tensions in the first tensioning member 340 and the second tensioning member 360 are maintained at a desired level of tensile force (e.g., within a target range of desired tensile force).

It should be understood that the force exerted by actuator 430 may be the prime moving force, so that instrument 330 insertion and withdrawal is directly controlled by actuator 430, and actuators 410,420 apply force sufficient to maintain tension in tension elements 340,360 and to maintain or change end effector 330's orientation as actuator 430 inserts and withdraws the instrument. And so, in one aspect actuator 430 controls instrument 300's insertion and withdrawal location while actuators 410,420 react to control tension on tension elements 340,360 as the location changes. For example, when actuator 430 slightly increases force to insert the instrument shaft, the slight tension increase in tension elements 340,360 is sensed and so actuators 410,420 decrease force to return tension elements 340,360 to the desired value. Alternatively, instrument 330 insertion and withdrawal is controlled by actuators 410,420,430 working in concert to control tension on tension elements 340,360 which in turn controls instrument 300's insertion and withdrawal location, and at the same time end effector 330's orientation is maintained or changed by actuators 410,420 working together to control relative tension between tension elements 340,360. For example, when actuator 430 slightly increases force to insert the instrument shaft, actuators 410,420 simultaneously decrease force to maintain tension in tension elements 340,360 at the desired value. It can be appreciated that these two tension-control aspects apply to a reverse situation in which actuators 410,420 act together to apply the prime moving force for insertion/withdrawal, with actuator 430 controlling tension in the tension members. And, it can be appreciated that these tension-control aspects apply to more complicated movements in which the instrument shaft is moved in insertion/withdrawal and the end effector is moved in one or more degrees of freedom.

Figure 11:
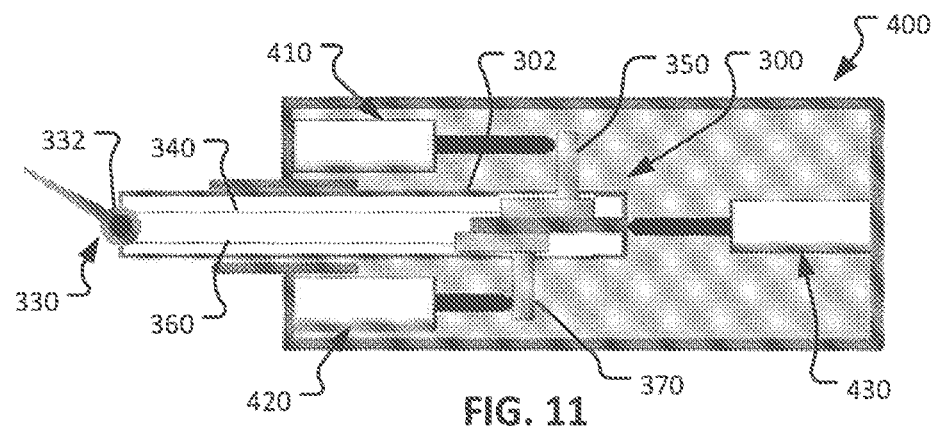
FIG. 11 is a schematic diagram of the instrument and drive system of FIG. 9 with the end effector oriented in an example pose.
Figure 12:
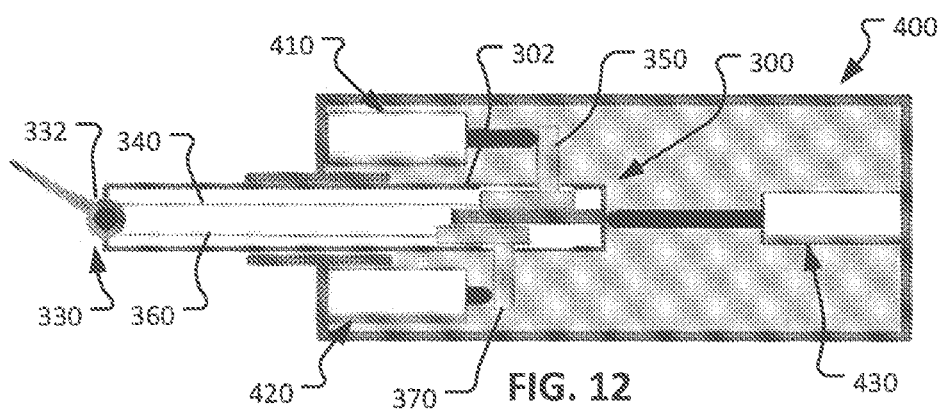
FIG. 12 is a schematic diagram of the instrument and drive system of FIG. 11 with the instrument extended distally in relation to the drive system while the end effector remains oriented in the example pose.
Figure 13:
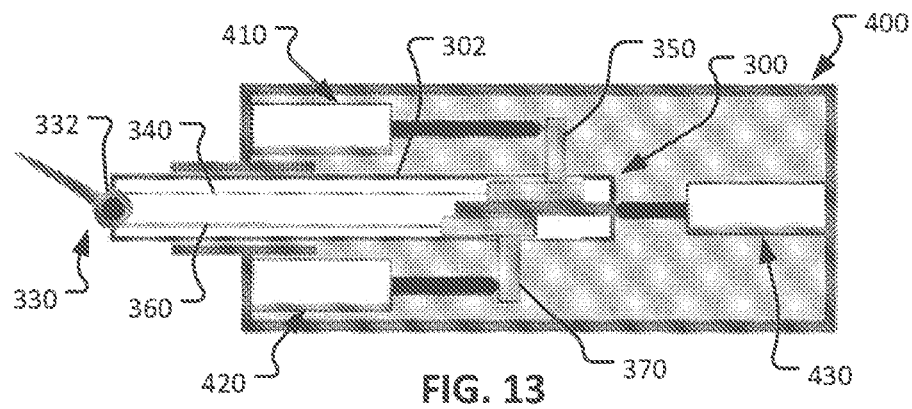
FIG. 13 is a schematic diagram of the instrument and drive system of FIG. 11 with the instrument retracted proximally in relation to the drive system while the end effector remains oriented in the example pose.

Referring also to FIGS. 11-13, the concepts described above can be further described by examples using illustrations of the surgical instrument 300 in various positions in relation to the instrument drive system 400.

In a first example, the arrangement of FIG. 9 can be transitioned to that of FIG. 11 by temporarily increasing the force exerted by the first actuator 410 to the first actuator engagement member 350 in comparison to the force exerted by the second actuator 420 to the second actuator engagement member 370, while the sum of the two forces is held equal to the force exerted by the shaft actuator 430 to the instrument shaft 302. In result, the end effector 330 will move in relation to the instrument shaft 302 while the surgical instrument 300 is maintained in a constant spatial relationship (i.e., no distal and proximal movements) in relation to the instrument drive 400. Such a movement can be made while the tensions in the first tensioning member 340 and the second tensioning member 360 are maintained at a desired level of tensile force (e.g., within a target range of desired tensile force).

In a second example, the arrangement of FIG. 9 can be transitioned to that of FIG. 12 by temporarily increasing the force exerted by the first actuator 410 to the first actuator engagement member 350 in comparison to the force exerted by the second actuator 420 to the second actuator engagement member 370, while the sum of the two forces is temporarily less than the force exerted by the shaft actuator 430 to the instrument shaft 302. In result, the end effector 330 will move in relation to the instrument shaft 302, and the surgical instrument 300 will extend distally in relation to the instrument drive 400. Such movements can be made while the tensions in the first tensioning member 340 and the second tensioning member 360 are maintained at a desired level of tensile force (e.g., within a target range of desired tensile force).

In a third example, the arrangement of FIG. 9 can be transitioned to that of FIG. 13 by temporarily increasing the force exerted by the first actuator 410 to the first actuator engagement member 350 in comparison to the force exerted by the second actuator 420 to the second actuator engagement member 370, while the sum of the two forces is temporarily greater than the force exerted by the shaft actuator 430 to the instrument shaft 302. In result, the end effector 330 will move in relation to the instrument shaft 302, and the surgical instrument 300 will retract proximally in relation to the instrument drive 400. Such movements can be made while the tensions in the first tensioning member 340 and the second tensioning member 360 are maintained at a desired level of tensile force (e.g., within a target range of desired tensile force).

In a fourth example, the arrangement of FIG. 12 can be transitioned to that of FIG. 13 by maintaining equal forces exerted by the first actuator 410 to the first actuator engagement member 350 and by the second actuator 420 exerted to the second actuator engagement member 370, while the sum of the two forces is temporarily greater than the force exerted by the shaft actuator 430 to the instrument shaft 302. In result, the end effector 330 will not move in relation to the instrument shaft 302, and the surgical instrument 300 will retract proximally in relation to the instrument drive 400. Such a movement can be made while the tensions in the first tensioning member 340 and the second tensioning member 360 are maintained at a desired level of tensile force (e.g., within a target range of desired tensile force).

In a fifth example, the arrangement of FIG. 13 can be transitioned to that of FIG. 12 by maintaining equal forces exerted by the first actuator 410 to the first actuator engagement member 350 and by the second actuator 420 exerted to the second actuator engagement member 370, while the sum of the two forces is temporarily less than the force exerted by the shaft actuator 430 to the instrument shaft 302. In result, the end effector 330 will move in relation to the instrument shaft 302, and the surgical instrument 300 will extend distally in relation to the instrument drive 400. Such a movement can be made while the tensions in the first tensioning member 340 and the second tensioning member 360 are maintained at a desired level of tensile force (e.g., within a target range of desired tensile force).

Examples so far have illustrated the drive unit's first and second actuators applying a proximal compressive force against their corresponding first and second actuator engagement members, and the drive unit's shaft actuator applying a distal compressive force against the instrument shaft. But, in another aspect the orientations of these forces are reversed, so that the drive unit's first and second actuators apply a distal compressive force against their corresponding first and second actuator engagement members, and the drive unit's shaft actuator applies a proximal compressive force against the instrument shaft. In this aspect, the tensioning members may be routed over pulleys so that distal movement of an actuator engagement member causes tension in the corresponding tension member and associated end effector movement. Or, the tensioning members may be replaced with compression members, such as push rods coupled to the end effector, so that distal movement of an actuator engagement member causes compression in the corresponding compression member and associated end effector movement.

Figure 14:
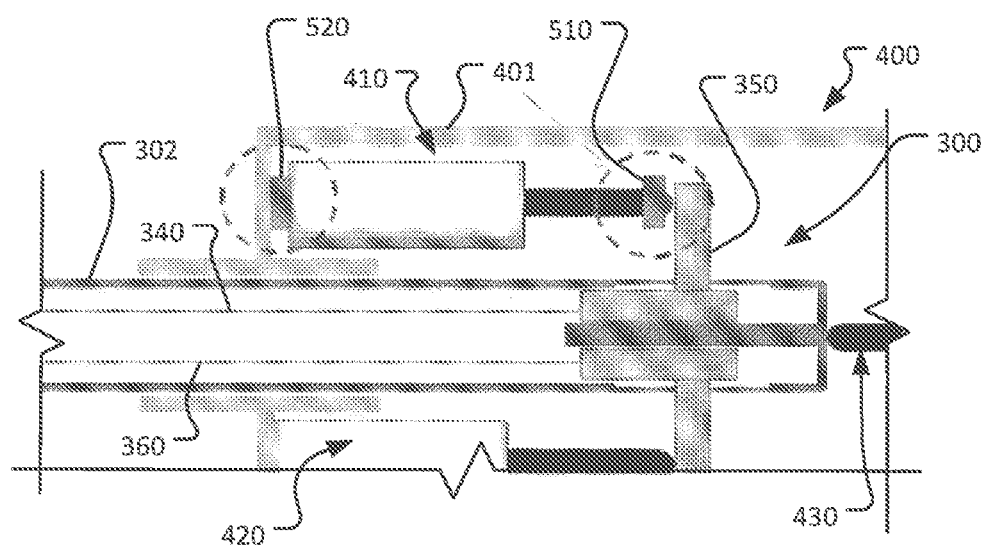
FIG. 14 is a schematic diagram of a portion of the instrument and drive system of FIG. 11 showing example locations of force sensors for detecting forces such as cable tension.

Referring to FIG. 14, in some embodiments the forces exerted by the actuators 410, 420, and/or 430 to the surgical instrument 300 can be detected by the use of one or more force detection devices. The output(s) of such force detection devices can be used for controlling the actuators 410, 420, and/or 430 (i.e., to control movements of the surgical instrument 300 and/or to control tensions of the first and second tensioning members 340 and 360).

In a first non-limiting example, the depicted arrangement includes a load cell 510 type of force sensor disposed at or near the juncture between the first actuator 410 and the first actuator engagement member 350. In another example, the depicted arrangement includes a load cell 520 type of force sensor disposed near the connection between the first actuator 410 and a structural member 401 of the instrument drive system 400. In some embodiments, the instrument drive system 400 can be a pod (i.e., readily interchangeable in relation to mounting on a manipulator assembly).

In some embodiments, other sensors and/or other devices can be used to detect the forces exerted by the actuators 410, 420, and/or 430 to the surgical instrument 300. For example, in some embodiments strain gauges can be located on the actuator engagement members, e.g., the first actuator engagement member 350. In another embodiment, the electrical current drawn by electric motors of the actuators 410, 420, and/or 430 can be measured and used as an indication of the forces exerted by the actuators 410, 420, and/or 430 to the surgical instrument 300. In some embodiments, a combination of such force detection devices and techniques can be used.

Referring to FIGS. 15-18, an example surgical instrument 600 that can be used as part of a computer-assisted teleoperated surgery system includes a proximal end portion 610, an instrument shaft 640, and an end effector 650. The surgical instrument 600 is an example of a surgical instrument that is configured in accordance with the schematic diagrams (e.g., FIGS. 8, 9, and 11-14) described above. Hence, the surgical instrument 600 can function in accordance with the schematic diagrams described above.

The instrument shaft 640 extends distally from the proximal end portion 610. The instrument shaft 640 includes a distal end portion to which the end effector 650 is coupled. The instrument shaft 640 defines a longitudinal axis 602 of the surgical instrument 600, along which the instrument is inserted into and withdrawn from the patient.

The end effectors (e.g., end effector 650) of the surgical instruments described herein can be any type of surgical end effector (e.g., graspers, cutters, cautery instruments, staplers, forceps, cameras, etc.). The end effectors (e.g., end effector 650) of the surgical instruments described herein can have one or multiple degrees of freedom (e.g., two, three, four, five, six, seven, eight, or more than eight degrees of freedom). Moreover, it should be understood that the concepts described herein in the context of a single degree of freedom of the end effectors can be extended to each degree of freedom of multiple degrees of freedom of the surgical instrument 600, and of other types of surgical instruments for computer-assisted tele-operated surgery systems.

In the depicted embodiment, the proximal end portion 610 includes a handle 612, a plurality of actuator engagement members (depicted here disposed in a grouping 630 at a same longitudinal location along the longitudinal axis 602), and an instrument shaft actuator engagement member 620. The plurality of actuator engagement members 630 are movably coupled to the proximal end portion 610. In the depicted embodiment, the plurality of actuator engagement members 630 are slidably coupled to the proximal end portion 610 such that the plurality of actuator engagement members 630 can translate parallel to the longitudinal axis 602. The instrument shaft actuator engagement member 620 is coupled to the proximal end portion 610. In the depicted embodiment, instrument shaft actuator engagement member 620 is pivotably coupled to the proximal end portion 610.

The handle 612 extends radially from the longitudinal axis 602. In the depicted embodiment, the handle 612 is the portion of proximal end portion 610 and of the entire surgical instrument 600 that radially extends the farthest. The handle 612 is configured to facilitate manual gripping and manipulation of the surgical instrument 600.

In some embodiments, the handle 612 includes an indicium that identifies the type of the surgical instrument 600. For example, in the depicted embodiment the handle 612 includes a visible indicium that is an icon 614 that depicts that the surgical instrument 600 is a grasper device. In some embodiments, the handle 612 includes a machine-readable indicium, such as an RFID chip or NFC tag that can be used to store and communicate information pertaining to the surgical instrument 600. For example, such information pertaining to the surgical instrument 600 can include, but is not limited to, a unique identification or serial number, the type of instrument, the number of times the instrument has been used for one or more surgical procedures, and the like.

In some embodiments, the handle 612 optionally includes one or more magnets that an instrument drive system can use to sense the presence of the surgical instrument 600 mounted in the instrument drive system.

The proximal end portion 610 includes the plurality of actuator engagement members. As depicted the actuator engagement members are disposed in a grouping 630 at a common longitudinal location along the longitudinal axis 602. Optionally they may be at two or more longitudinal locations along longitudinal axis 602 so that a first coupled pair of actuator engagement members is at a first longitudinal location and a second coupled pair of actuator engagement members is at a second longitudinal location, or each actuator engagement member of a coupled pair is at a different longitudinal location. The actuator engagement members are configured to releasably engage with actuators which drive the actuator engagement members and corresponding movements of the end effector 650 as described above in reference to FIGS. 8-14. As shown, each individual actuator engagement member slides longitudinally in a corresponding individual longitudinal slot in proximal end portion 610. In other optional aspects, however, an individual actuator engagement member may have a different configuration (e.g., a lever, a rotating piece such as a disk or gear, a cam surface, and the like). As shown, all individual actuator engagement members extend radially outward slightly beyond the outer perimeter of proximal end portion 610 so that the associated actuators to not extend into proximal end portion 610. Alternatively, one or more individual actuator engagement members may not extend to or beyond the outer perimeter of proximal end portion (e.g., they are positioned slightly inside proximal end portion 610) so they are less prone to damage or do not snag on an object. In this alternative configuration, the associated actuators extend slightly into proximal end portion 610 to engage the instrument's actuator engagement members. All actuator engagement members may have the same configuration, or two or more actuator engagement member configurations may be used in a single instrument, as long as the actuator engagement members comply with the principles of operation described with reference to FIGS. 8-14. In the depicted embodiment the following example actuator engagement members are included: 632a, 632b, 634a, 634b, 636a, 636b, and 638. More or fewer actuator engagement members may be included in some embodiments.

The actuator engagement members, e.g., actuator engagement members 632a, 632b, 634a, 634b, 636a, 636b, and 638, are coupled to tensioning members (e.g., comprising flexible cables that can be routed over small radius pulleys (e.g., 2-10 mm scale), semi-flexible cables that cannot be routed over small radius pulleys, rigid hypo-tubes, pull rods, etc.) that extend along the instrument shaft 640 and that are movably coupled to the end effector 650. Hence, movements of the actuator engagement members result in movements of the end effector 650.

In some cases, the actuator engagement members are paired (e.g., actuator engagement members 632a and 632b, actuator engagement members 634a and 634b, and actuator engagement members 636a and 636b) such that moving one actuator engagement member of the pair proximally results in a corresponding distal movement of the other actuator engagement member of the pair. For example, moving actuator engagement member 632a proximally results in a corresponding distal movement of actuator engagement member 632b, and moving actuator engagement member 632b proximally results in a corresponding distal movement of actuator engagement member 632a. In other words, actuator engagement member pairs move in opposition to each other.

When the structure of the surgical instrument 600 includes actuator engagement members (e.g., actuator engagement members 632a, 632b, 634a, 634b, 636a, 636b, and 638) that are coupled to flexible tensioning cables, it can be envisioned that distal movements of the actuator engagement members without a corresponding proximal movement of a paired actuator engagement member will not move the end effector 650. Rather, the flexible tensioning cable attached to the actuator engagement member being moved distally would simply become flaccid (due to the limited column strength/rigidity of a flexible tensioning cable). Hence, it can be said that, in some embodiments, the actuator engagement members 632a, 632b, 634a, 634b, 636a, 636b, and 638 are configured to move the end effector 650 in response to receiving a proximally-directed force, and are configured to not move the end effector 650 in response to receiving a distally-directed force. However, in some embodiments one or more of the actuator engagement members (e.g., the actuator engagement member 638 which is not paired with another actuator engagement member) are configured to move the end effector 650 both ways (proximally and distally). That is, such actuator engagement members optionally drive a flexible or semi-flexible member in a manner similar to Bowdin cable operation, or drive a rigid member in a manner similar to push/pull rod operation. For example, in some embodiments the actuator engagement member 638 may be configured to operate a blade of the end effector 650 or a clamp in the case that the end effector 650 includes a stapler. In the example of the blade, the actuator engagement member 638 works opposite to a spring (cut under drive, spring back). In the example of the stapler, the actuator engagement member 638 moves distally to drive the firing sequence, while the grip-open actuation returns the actuator engagement member 638 proximally.

Still referring to FIGS. 15-18, in the depicted arrangement of surgical instrument 600, the actuator engagement members 632a, 632b, 634a, 634b, 636a, 636b, and 638 are all positioned at the same longitudinal location along the longitudinal axis 602 of the surgical instrument. However, during use of the surgical instrument 600, the actuator engagement members 632a, 632b, 634a, 634b, 636a, 636b, and 638 are moved to various longitudinal locations along the longitudinal axis 602 of the surgical instrument. This is described further by the following example.

When the surgical instrument 600 is coupled with an instrument drive system, actuators of the instrument drive system will releasably couple with the actuator engagement members 632a, 632b, 634a, 634b, 636a, 636b, and 638. For example, the actuators will engage the actuator engagement members by moving proximally until a reaction force that indicates engagement is sensed. For paired actuator engagement members 632a and 632b, a first actuator moves proximally until actuator engagement member 632a is engaged, and a second actuator moves proximally until actuator engagement member 632b is engaged. The first and second actuators may then adjust the longitudinal position of the corresponding actuator engagement members 632a and 632b to set a desired tension in corresponding paired tension members coupled to the distal end component so that all slack or backlash is removed from the drive train between the actuator engagement members and the corresponding distal end component and so that movement of the actuator engagement members results in immediate movement of the corresponding distal end component. That is, one or more instrument drive system actuators engage the corresponding one or more instrument actuator engagement members and set a dynamic preload tension (which may be in addition to the static preload tension described below) in the one or more instrument tension members between the one or more actuator engagement members and the corresponding instrument distal end component (e.g., wrist or end effector component).

Then, in response to input (such as from surgeon console 40 of FIG. 2), the actuators of the instrument drive system correspondingly move some or all of the actuator engagement members (e.g., the actuator engagement members 632a, 632b, 634a, 634b, 636a, and/or 636b) proximally to initiate desired movements of the end effector 650 or other distal end component. For example, for paired actuator engagement members 632a and 632b, a first actuator of the instrument drive system may move actuator engagement member 632a proximally. In concert with that proximal movement of actuator engagement member 632a, a second actuator of the instrument drive system may resist distal movement of actuator engagement member 632b, thus keeping tension on actuator engagement member 632b's corresponding tension member, but still allows actuator engagement member 632b to move distally. The second actuator's resistance to actuator engagement member 632b's distal movement is modulated to maintain a desired tension in the tensioning members that correspond to the actuator engagement members 632a and 632b. This operation is performed in accordance with the dynamic tensioning concepts described above in reference to FIGS. 8-14.

In one aspect, the control system controls the tension in each of the paired tension members to be equal as the tension members move the corresponding end effector. In another aspect, however, the control system controls the tension in the tension members to cause a required load force in the loaded tension member and to maintain a minimum tension on the non-loaded tension member.

To explain this differential force aspect by example, consider paired actuator engagement members 632a and 632b. When their associated end effector is at a neutral position (e.g., centered on the instrument's longitudinal axis and not engaged with another object), not moving, and not experiencing a load, the control system may cause an equal force to be applied to actuator engagement members 632a and 632b. This equal force is at or above a minimum force required to remove backlash from the tension member connections between the end effector and the actuator engagement members for effective control. But, the equal force is kept low in order to reduce friction and tension loads that result in mechanical wear.

To move the associated end effector, the control system moves the actuator engagement members 632a and 632b in opposite directions. The end effector movement caused by the proximal motion of actuator engagement member 632a may be unresisted (e.g., the end effector moves freely) or resisted (e.g., the end effector moves against tissue or another part of the end effector, such as a jaw moving against another jaw in grip). Friction in the drive train may also cause a load that requires a higher force be applied to actuator engagement member 632a than is required to keep the end effector under effective control at a neutral position. Thus, the actuator associated with actuator engagement member 632a must increase its force against actuator engagement member 632 to either continue to move the corresponding end effector or to maintain the corresponding end effector's force against the resistance. In this situation, however, there is no need for the actuator associated with the paired actuator engagement member 632b to exert a force on actuator engagement member 632b that is the same as the force exerted on actuator engagement member 632a. What is required is that the force exerted on actuator engagement member 632b be at or above a minimum threshold necessary to keep the associated tension member from going slack or deviating from its path, such as by leaving a pulley.

As a further illustration, if the control system causes actuator engagement member 632a to receive a maximum allowable force from its associated drive unit actuator in order to produce a maximum force at the corresponding end effector (e.g., to produce a maximum possible end effector grip force), then the control system may cause actuator engagement member 632b to receive only a minimum force required to ensure that its associated tension member does not go slack and does not disengage from its proper routing, or to receive a force between this minimum force and the force applied to actuator engagement member 632a. And, although this aspect applies for maximum force applied to actuator engagement member 632a, it also applies when lower forces are applied so that again the conflicting tension caused by the force against actuator engagement member 632b is minimized. It should be understood that if the end effector is then to be moved in the opposite direction, the required load force is applied against actuator engagement member 632b, and the required tension-maintaining force is applied against actuator engagement member 632a. It should also be understood that this differential force aspect applies if compression is used to move an end effector instead of tension, so that any unnecessary compression force is reduced or minimized.

In some embodiments of surgical instrument 600, pre-load tensioning members (e.g., springs 633) may be included to maintain a minimal tension in the tensioning members while the surgical instrument 600 is separated from an instrument drive system—a static preload tension. Such minimal pre-tensioning may help ensure that the tensioning members remain oriented and routed within the surgical instrument 600 as desired. In the depicted embodiment, compression springs 633 apply a proximally-directed force to the actuator engagement members 632a, 632b, 634a, 634b, 636a, 636b, and 638 to maintain a minimal tension in the tensioning members while the surgical instrument 600 is separated from an instrument drive system. In some embodiments, other types of pre-load tensioning members may be used such as, but not limited to, flexures created as part of shaft 640 or proximal end portion 610, extension springs, torsion springs, leaf springs, and the like. Further, in embodiments that incorporate compression members in place of tensioning members, pre-load compression members similar to these pre-load tensioning members may be used to eliminate mechanical backlash in the drive trains between actuator engagement members and the end effector.

Still referring to FIGS. 15-18, proximal end portion 610 includes the instrument shaft actuator engagement member 620. The instrument shaft actuator engagement member 620 is used for releasably coupling the proximal end portion 610 to an actuator of an instrument drive system. Since the instrument shaft 640 is rigidly coupled to the proximal end portion 610, the instrument shaft actuator engagement member 620 also releasably couples the instrument shaft 640 to an actuator of an instrument drive system. This concept of using the instrument shaft actuator engagement member 620 to couple an actuator to the proximal end portion 610 and the instrument shaft 640 was introduced above by the schematic diagrams and the descriptions thereof (e.g., by FIG. 9 which includes the shaft actuator 430 that can releasably couple with the instrument shaft 302). Hence, the instrument shaft actuator engagement member 620, when coupled with an actuator of an instrument drive system, is used for moving the entire surgical instrument 600 proximally and/or distally in relation to the instrument drive system. In addition (as described in reference to the force diagram of FIG. 10), the instrument shaft actuator engagement member 620, when coupled with an actuator of an instrument drive system, is used for balancing proximally directed forces applied by actuators to the actuator engagement members 632a, 632b, 634a, 634b, 636a, 636b, and 638.

In the depicted embodiment, the actuator engagement members 632a, 632b, 634a, 634b, 636a, 636b, and 638 are configured to receive proximally-directed forces from the actuators of an instrument drive system but are not configured to receive distally-directed forces from the actuators of an instrument drive system. In other words, the actuator engagement members 632a, 632b, 634a, 634b, 636a, 636b, and 638 are not detained (not immovably coupled with; a non-detained engagement) to the actuators of an instrument drive system. Stated differently, the actuator engagement members 632a, 632b, 634a, 634b, 636a, 636b, and 638 are each configured for directly facilitating (causing) movement the end effector 650 in response to receiving a proximally-directed force from a corresponding actuator, and are each not configured for directly facilitating movement the end effector 650 in response to receiving a distally-directed force from a corresponding actuator. In contrast, in the depicted embodiment the instrument shaft actuator engagement member 620 is configured to directly facilitate movement of the entire surgical instrument 600 proximally in response to receiving a proximally-directed force, and is configured to directly facilitate movement of the entire surgical instrument 600 distally in response to receiving a distally-directed force. That is the case because the instrument shaft actuator engagement member 620 is configured to be releasably detained to an actuator of an instrument drive system. For example, in the depicted embodiment the instrument shaft actuator engagement member 620 is a latch mechanism that can be used to releasably detain the proximal end portion 610 and the instrument shaft 640 to an actuator of an instrument drive system. It should be understood that the use of a latch mechanism for the instrument shaft actuator engagement member 620 is not required in all embodiments, and other suitable coupling mechanisms at various locations on the instrument may be used.

Further, in some embodiments the instrument shaft actuator engagement member 620 is configured such that the instrument drive system only exerts distally-directed forces to the surgical instrument 600 (i.e., not proximally-directed forces). The dynamic tension and position control concepts described herein can still be performed in such a case where the instrument shaft actuator engagement member 620 is configured to receive only a distally-directed force from the instrument drive system. In this aspect, distally-directed force on the instrument's shaft actuator engagement member is balanced with proximally-directed forces on the instrument's actuator engagement members.

Referring particularly to FIG. 18, in some embodiments the surgical instrument 600 is configured with one or more connectors or contacts for inputting energy to the end effector 650 (e.g., energy for cauterization). For example, in some embodiments the surgical instrument may be configured to use monopolar RF, bi-polar RF, or another energy form. In such a case, in some embodiments the one or more connectors are located on a proximal area 613 of the handle 612. Such a location can allow the one or more connectors to be readily accessible for connection with one or more cables that supply the energy. Such a location can also allow the connections to be made and/or disconnected while the surgical instrument 600 is coupled with an instrument drive system.

Figure 19:
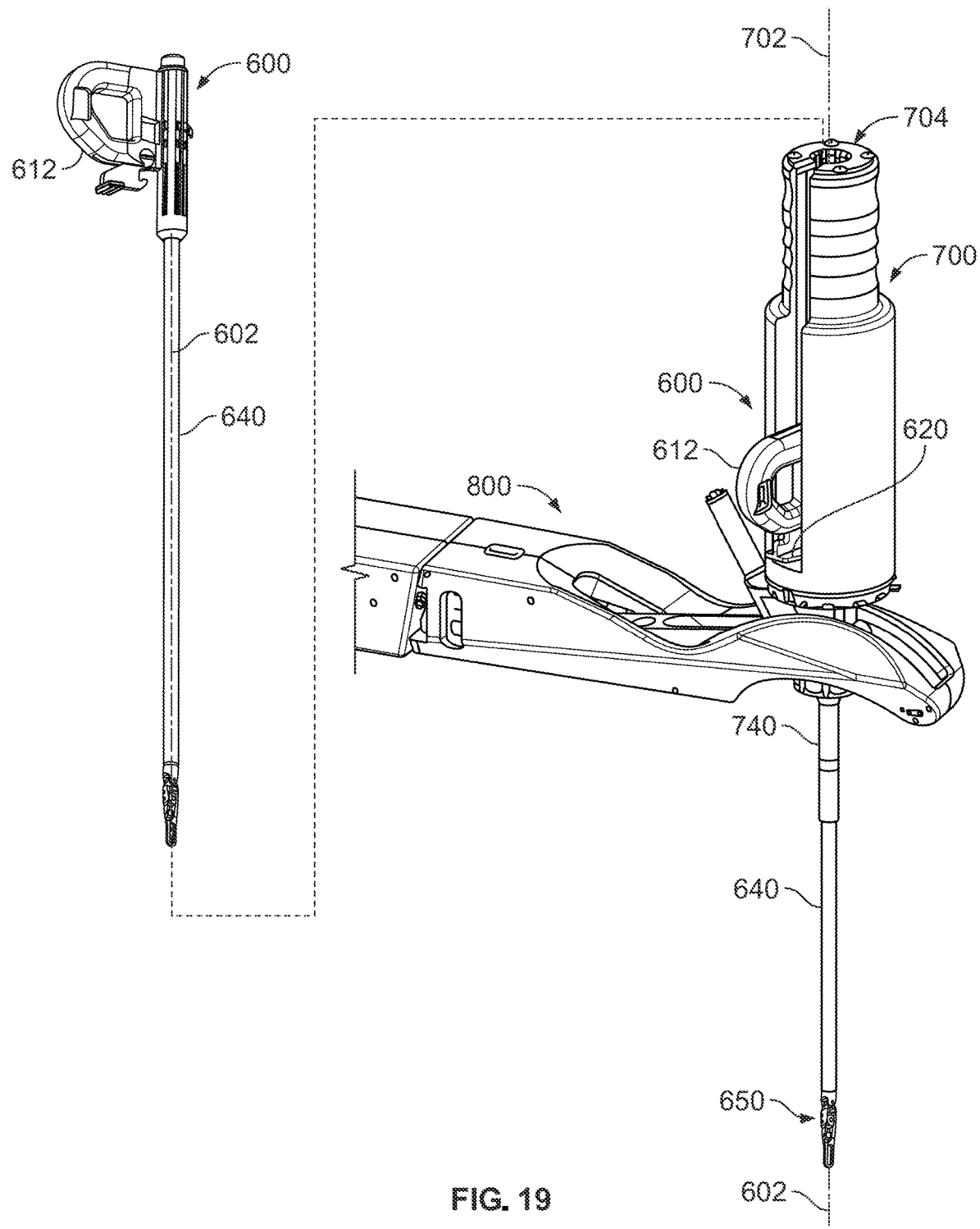
FIG. 19 depicts how the surgical instrument of FIG. 15 can be coupled with an example instrument drive system in accordance with some embodiments.

Referring to FIG. 19, the surgical instrument 600 can be selectively coupled with a compatible instrument drive system 700 (also referred to as pod 700) that defines a longitudinal axis 702 of a space configured to receive the surgical instrument 600. In accordance with a typical implementation for computer-assisted tele-operated surgery, the instrument drive system 700 can be coupled to a manipulator assembly 800 with multiple degrees of freedom. In some embodiments, the pod 700 is readily detachable from the manipulator assembly 800 such that the pod 700 can be conveniently interchanged with another pod. The manipulator assembly 800 can be attached to a supporting structure of various types (e.g., refer to FIGS. 3 and 4). The instrument shaft 640 can slidably extend through a cannula 740 that is optionally releasably mounted to the manipulator assembly 800 or to the instrument drive system 700.

In the depicted embodiment, the surgical instrument 600 can be releasably coupled with the instrument drive system 700 by moving the surgical instrument 600 distally into an opening at the proximal end 704 of the instrument drive system 700. In particular, the longitudinal axis 602 of the surgical instrument 600 can first be aligned with the longitudinal axis 702 of the instrument drive system 700. Then the surgical instrument 600 can be slid distally in relation to the instrument drive system 700 until the instrument shaft engagement member 620 couples with the instrument drive system 700.

At least portions of the handle 612 and the instrument shaft engagement member 620 extend farther radially than adjacent portions of the instrument drive system 700 while the surgical instrument is coupled with the instrument drive system, so that handle 612 protrudes out of pod 700. Accordingly, the handle 612 and instrument shaft engagement member 620 are accessible to the hands of a user. Such accessibility can advantageously facilitate ready decoupling of the surgical instrument 600 from the instrument drive system 700.

Although not visible, the instrument drive system 700 includes multiple actuators (schematically depicted in FIGS. 9 and 11-14) that releasably couple with the actuator engagement members 632*a*, 632*b*, 634*a*, 634*b*, 636*a*, 636*b*, and 638 while the surgical instrument 600 is coupled with the instrument drive system 700. In some embodiments, the actuators are linear actuators that include lead screws and lead screw nut members, and other suitable linear actuators (e.g., chain, belt, hydraulic, pneumatic, electromagnetic, and the like) may be used. In some embodiments, non-linear actuators such as rotary actuators, or combinations of linear and non-linear actuators, may be used to produce the antagonistic force aspects as described. In some embodiments, one or more force sensors are included in the instrument drive system 700 by which forces applied to the actuator engagement members 632*a*, 632*b*, 634*a*, 634*b*, 636*a*, 636*b*, and/or 638 can be determined and fed back to the processor 43 (FIG. 2).

In some embodiments, the entirety of the surgical instrument 600 coupled to the instrument drive system 700 can be rotated or rolled about the longitudinal axes 602 and 702 as a single unit. The instrument actuator engagement member 620, when coupled to pod 700 either via an instrument shaft insertion/withdrawal actuator or directly to pod 700, is used to secure the instrument shaft during roll around longitudinal axis 602 as pod 700 rotates around its longitudinal axis 702. In addition, handle 612 may provide extra support against pod 700 for roll. A motor at the distal end of pod 700, either inside pod 700 or part of manipulator 800, rotates the assembly of pod 700 and instrument 600. Thus the instrument shaft, and the distal end effector, may be simultaneously inserted/withdrawn and rolled.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A medical system comprising:
    a surgical instrument comprising:
        a handle;
        a shaft having a proximal end portion and a distal end portion;
        an end effector movably coupled to the distal end portion;
        one or more cables coupled to the end effector and extending along the shaft; and
        a plurality of actuator engagement members respectively coupled to the one or more cables, wherein movements of the actuator engagement members cause motions of the end effector; and
    a surgical instrument drive unit operably coupled to a manipulator arm of a robotic surgery system and defining an opening and a space along a longitudinal axis of the surgical instrument drive unit, wherein the opening and the space slidably receive the shaft of the surgical instrument as the surgical instrument is releasably coupled with the surgical instrument drive unit, the surgical instrument drive unit comprising:
        a plurality of actuators, each of the actuators being releasably coupled with one of the actuator engagement members while the surgical instrument is coupled with the surgical instrument drive unit, the actuators being controllable to drive the movements of the actuator engagement members that cause the motions of the end effector; and
        a shaft insertion actuator releasably coupleable with the surgical instrument, the shaft insertion actuator being controllable to force the shaft of the surgical instrument to distally extend along the longitudinal axis relative to the surgical instrument drive unit,
        wherein the one or more cables coupled to the end effector are controllable to force the shaft of the surgical instrument to proximally retract along the longitudinal axis relative to the surgical instrument drive unit.

2. The medical system of claim 1, wherein the actuator engagement members of the surgical instrument are rotary members.

3. The medical system of claim 2, wherein the actuators of the instrument drive system are rotary actuators.

4. The medical system of claim 1, wherein the surgical instrument drive unit further comprises a rotation actuator that is controllable to drive the handle of the surgical instrument to roll about the longitudinal axis of the surgical instrument drive unit.

5. The medical system of claim 1, wherein the surgical instrument drive unit further comprises a rotation actuator that is controllable to drive the actuator engagement members of the surgical instrument to roll about the longitudinal axis of the surgical instrument drive unit.

6. The medical system of claim 1, wherein the actuator engagement members are translatable relative to the instrument shaft.

7. The medical system of claim 1, wherein the actuator engagement members are translatable relative to, and parallel to, the instrument shaft.

8. The medical system of claim 1, wherein, while the surgical instrument is coupled with the surgical instrument drive unit, the shaft of the surgical instrument extends through the surgical instrument drive unit.

9. The medical system of claim 1, wherein the one or more cables are within the shaft.

10. The medical system of claim 1, wherein the handle is configured to physically latch the surgical instrument to the surgical instrument drive unit.

11. The medical system of claim 1, wherein portions of the actuators contact and releasably couple with the actuator engagement members, and wherein the portions of the actuators translate relative to the longitudinal axis.

12. The medical system of claim 1, further comprising one or more springs arranged to tension the one or more cables.

13. The medical system of claim 1, wherein the surgical instrument drive unit includes an outer housing and a rotation actuator that is controllable to drive the handle of the surgical instrument to roll about the longitudinal axis of the surgical instrument drive unit, and wherein the actuators, the shaft insertion actuator, and the rotation actuator are all located within the outer housing.

14. The medical system of claim 1, wherein at least portion of the surgical instrument drive unit rotates about the longitudinal axis as the surgical instrument is rotated about the longitudinal axis.

15. The medical system of claim 1, wherein the handle extends radially from the shaft of the surgical instrument.

* * * * *